US011896689B2

(12) United States Patent
Dunlop et al.

(10) Patent No.: US 11,896,689 B2
(45) Date of Patent: Feb. 13, 2024

(54) METHOD OF MAKING A CLEAR PERSONAL CARE COMPRISING MICROCAPSULES

(71) Applicant: The Procter & Gamble Company, Cincinnati, OH (US)

(72) Inventors: David Scott Dunlop, Mason, OH (US); Eric Shawn Goudy, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 550 days.

(21) Appl. No.: 16/907,711

(22) Filed: Jun. 22, 2020

(65) Prior Publication Data

US 2021/0045979 A1 Feb. 18, 2021

Related U.S. Application Data

(60) Provisional application No. 62/867,974, filed on Jun. 28, 2019.

(51) Int. Cl.
*A61K 8/11* (2006.01)
*A61K 8/34* (2006.01)
(Continued)

(52) U.S. Cl.
CPC ............... *A61K 8/11* (2013.01); *A61K 8/342* (2013.01); *A61K 8/416* (2013.01); *A61K 8/463* (2013.01);
(Continued)

(58) Field of Classification Search
CPC .......... A61K 8/11; A61K 8/342; A61K 8/416; A61K 8/463; A61K 8/602; A61K 8/73;
(Continued)

(56) References Cited

U.S. PATENT DOCUMENTS

| 1,094,935 A | 4/1914 | Schenck et al. |
| 2,280,271 A * | 4/1942 | Sullivan .................. F04C 14/24 |
| | | 417/252 |

(Continued)

FOREIGN PATENT DOCUMENTS

| AU | 2012337567 B2 | 4/2017 |
| CA | 2143558 A1 | 8/1996 |

(Continued)

OTHER PUBLICATIONS

All Office Actions; U.S. Appl. No. 17/184,814, filed Feb. 25, 2021.

(Continued)

*Primary Examiner* — Charles Cooley
(74) *Attorney, Agent, or Firm* — John G. Powell; Angela Kathryn Haughey

(57) ABSTRACT

A method of making a personal care composition that involves using a mixer to combine a personal care composition chassis with microcapsules. The mixer has a housing, a first fluid inlet, a second inlet, a fluid outlet and a rotor connected to the housing. The rotor has blades positioned within the housing to define cells between neighboring blades and the housing. The personal care composition chassis, which includes surfactants and water, is advanced along a flow path from the first fluid inlet toward the fluid outlet, while the microcapsules are transferred from the second inlet to the flow path by rotating the rotor. Air in the microcapsule composition is directed from inside the cells toward the second inlet, and the microcapsule composition is combined with the personal care composition chassis to form the personal care composition. The personal care composition is advanced from the outlet.

26 Claims, 11 Drawing Sheets

(51) Int. Cl.
<table>
<tr><td>A61K 8/41</td><td>(2006.01)</td></tr>
<tr><td>A61K 8/46</td><td>(2006.01)</td></tr>
<tr><td>A61K 8/60</td><td>(2006.01)</td></tr>
<tr><td>A61K 8/73</td><td>(2006.01)</td></tr>
<tr><td>A61K 8/81</td><td>(2006.01)</td></tr>
<tr><td>A61Q 5/02</td><td>(2006.01)</td></tr>
<tr><td>B01J 13/08</td><td>(2006.01)</td></tr>
<tr><td>B01F 25/314</td><td>(2022.01)</td></tr>
<tr><td>B01F 35/71</td><td>(2022.01)</td></tr>
<tr><td>B01F 27/093</td><td>(2022.01)</td></tr>
<tr><td>B01F 35/00</td><td>(2022.01)</td></tr>
</table>

(52) U.S. Cl.
CPC ............... *A61K 8/602* (2013.01); *A61K 8/73* (2013.01); *A61K 8/731* (2013.01); *A61K 8/733* (2013.01); *A61K 8/8129* (2013.01); *A61Q 5/02* (2013.01); *B01F 25/31433* (2022.01); *B01F 27/093* (2022.01); *B01F 35/189* (2022.01); *B01F 35/71411* (2022.01); *B01J 13/08* (2013.01); *A61K 2800/262* (2013.01); *A61K 2800/412* (2013.01); *A61K 2800/805* (2013.01)

(58) Field of Classification Search
CPC ...... A61K 8/731; A61K 8/733; A61K 8/8129; A61K 2800/262; A61K 2800/412; A61K 2800/805; A61K 8/042; A61K 2800/56; A61K 8/34; A61K 8/37; A61K 8/678; A61K 8/922; A61K 2800/10; A61Q 5/02; A61Q 19/10; A61Q 19/00; B01F 25/31433; B01F 27/093; B01F 35/189; B01F 35/71411; B01F 35/7176; B01J 13/08

See application file for complete search history.

(56) References Cited

U.S. PATENT DOCUMENTS

| | | | |
|---|---|---|---|
| 2,280,272 A * | 4/1942 | Sullivan | B01F 25/60 417/252 |
| 2,326,733 A | 8/1943 | Fisher | |
| 2,396,278 A | 3/1946 | Otto | |
| 2,438,091 A | 3/1948 | Lynch | |
| 2,486,921 A | 11/1949 | Byerly | |
| 2,486,922 A | 11/1949 | Bruce | |
| 2,528,378 A | 10/1950 | McCabe, Jr. | |
| 2,658,072 A | 11/1953 | Kosmin | |
| 2,694,668 A | 11/1954 | Fricke | |
| 2,757,049 A * | 7/1956 | Temple | B65G 53/4633 406/67 |
| 2,786,847 A | 3/1957 | Cislak | |
| 2,798,053 A | 7/1957 | Brown | |
| 2,809,971 A | 10/1957 | Jack | |
| 2,826,551 A | 3/1958 | Geen | |
| 3,152,046 A | 10/1964 | Maria | |
| 3,155,591 A | 11/1964 | Harry | |
| 3,194,540 A * | 7/1965 | Hager | B01F 27/2711 241/86 |
| 3,236,733 A | 2/1966 | Karsten | |
| 3,332,880 A | 7/1967 | Adriaan | |
| 3,589,999 A | 6/1971 | Mcrae | |
| 3,590,035 A | 6/1971 | Damico | |
| 3,626,265 A * | 12/1971 | Kraakman | F04C 2/3446 418/266 |
| 3,655,096 A | 4/1972 | Easter | |
| 3,753,196 A | 8/1973 | Kurtz | |
| 3,761,418 A | 9/1973 | Parran | |
| 3,773,770 A | 11/1973 | Damico | |
| 3,821,963 A * | 7/1974 | Olson | F04B 13/02 137/99 |
| 3,852,441 A | 12/1974 | Kooistra | |
| 3,929,678 A | 12/1975 | Laughlin et al. | |
| 3,940,482 A | 2/1976 | Grand | |
| 3,958,581 A | 5/1976 | Abegg | |
| 3,959,461 A | 5/1976 | Bailey | |
| 3,964,500 A | 6/1976 | Drakoff | |
| 4,055,655 A | 10/1977 | Maurer | |
| 4,089,945 A | 5/1978 | Brinkman | |
| 4,152,416 A | 5/1979 | Marra | |
| 4,161,426 A | 7/1979 | Kneer | |
| 4,197,865 A | 4/1980 | Jacquet | |
| 4,217,914 A | 8/1980 | Jacquet | |
| 4,323,683 A | 4/1982 | Bolich, Jr | |
| 4,345,080 A | 8/1982 | Bolich, Jr. | |
| 4,364,387 A | 12/1982 | Larkin | |
| 4,379,753 A | 4/1983 | Bolich, Jr. | |
| 4,381,919 A | 5/1983 | Jacquet | |
| 4,387,090 A | 6/1983 | Bolich, Jr. | |
| 4,422,853 A | 12/1983 | Jacquet | |
| 4,470,982 A | 9/1984 | Winkler | |
| 4,507,280 A | 3/1985 | Pohl | |
| 4,529,586 A | 7/1985 | De | |
| 4,565,647 A | 1/1986 | Llenado | |
| 4,604,272 A | 8/1986 | Kratel | |
| 4,608,183 A | 8/1986 | Rossmoore | |
| 4,663,158 A | 5/1987 | Wolfram | |
| 4,666,616 A | 5/1987 | Rossmoore | |
| 4,670,430 A | 6/1987 | Imamura | |
| 4,686,254 A | 8/1987 | Lochhead | |
| 4,704,272 A | 11/1987 | Oh | |
| 4,708,863 A | 11/1987 | Bews | |
| 4,726,915 A | 2/1988 | Verdicchio | |
| 4,788,006 A | 11/1988 | Bolich, Jr. | |
| 4,834,767 A | 5/1989 | Helioff | |
| 4,885,107 A | 12/1989 | Wetzel | |
| 4,898,585 A | 2/1990 | Borsanyi | |
| 4,995,804 A * | 2/1991 | Hirabayashi | B30B 11/003 418/210 |
| 5,034,218 A | 7/1991 | Duvel | |
| 5,057,153 A | 10/1991 | Ruggiero | |
| 5,104,646 A | 4/1992 | Bolich, Jr. | |
| 5,106,609 A | 4/1992 | Bolich, Jr. | |
| 5,106,613 A | 4/1992 | Hartnett | |
| 5,114,898 A | 5/1992 | Pinnavaia | |
| 5,154,847 A | 10/1992 | Lapetina | |
| 5,186,928 A | 2/1993 | Birtwistle | |
| 5,202,048 A | 4/1993 | Bartolo | |
| 5,227,156 A | 7/1993 | Wiese | |
| 5,248,445 A | 9/1993 | Rizvi | |
| 5,273,189 A | 12/1993 | Jouillat et al. | |
| RE34,584 E | 4/1994 | Grote | |
| 5,358,667 A | 10/1994 | Bergmann | |
| 5,360,581 A | 11/1994 | Rizvi | |
| 5,373,973 A | 12/1994 | Foster | |
| 5,462,589 A | 10/1995 | Nicholas | |
| 5,466,425 A | 11/1995 | Adams | |
| 5,478,501 A | 12/1995 | Rau | |
| 5,495,538 A | 2/1996 | Fan | |
| 5,518,774 A | 5/1996 | Kappock | |
| 5,540,954 A | 7/1996 | Nicholas | |
| 5,562,995 A | 10/1996 | Kappock | |
| 5,609,862 A | 3/1997 | Chen et al. | |
| 5,614,538 A | 3/1997 | Nelson, Jr. | |
| 5,674,478 A | 10/1997 | Dodd et al. | |
| 5,696,169 A | 12/1997 | Otsu | |
| 5,710,114 A | 1/1998 | Pyles | |
| 5,720,550 A * | 2/1998 | Akiyama | B65B 1/26 366/139 |
| 5,726,137 A | 3/1998 | Patel | |
| 5,750,122 A | 5/1998 | Evans | |
| 5,756,076 A | 5/1998 | Cervantes | |
| 5,776,444 A | 7/1998 | Birtwistle et al. | |
| 5,785,962 A | 7/1998 | Hinz | |
| 5,798,121 A | 8/1998 | Cauwet | |
| 5,811,487 A | 9/1998 | Schulz, Jr. et al. | |
| 5,836,479 A | 11/1998 | Klima et al. | |
| 5,837,661 A | 11/1998 | Evans | |
| 5,853,707 A | 12/1998 | Wells | |
| 5,854,319 A | 12/1998 | Olenick, Jr. | |
| 5,874,476 A | 2/1999 | Hsu | |
| 5,876,705 A | 3/1999 | Uchiyama | |

(56) References Cited

U.S. PATENT DOCUMENTS

| | | | |
|---|---|---|---|
| 5,880,076 A | 3/1999 | Vermeer | |
| 5,883,154 A | 3/1999 | Kappock | |
| 5,885,948 A | 3/1999 | Glenn, Jr. et al. | |
| 5,939,059 A | 8/1999 | Franklin | |
| 5,939,203 A | 8/1999 | Kappock | |
| 5,955,066 A | 9/1999 | Sako | |
| 5,965,515 A | 10/1999 | Rau | |
| 5,971,604 A * | 10/1999 | Linga | B01F 35/718051 251/207 |
| 5,977,036 A | 11/1999 | Guskey | |
| 5,997,036 A | 12/1999 | Hamada | |
| 5,997,851 A | 12/1999 | Cox | |
| 6,017,562 A | 1/2000 | Kaufman | |
| 6,034,043 A | 3/2000 | Fujiwara | |
| 6,183,766 B1 | 2/2001 | Sine et al. | |
| 6,303,109 B1 | 10/2001 | Foerster | |
| 6,309,628 B1 | 10/2001 | Ansmann | |
| 6,333,040 B1 | 12/2001 | Boyxen | |
| 6,354,729 B1 * | 3/2002 | Brown | F04C 2/344 366/307 |
| RE37,793 E | 7/2002 | Domenico | |
| 6,432,420 B2 | 8/2002 | Ellis | |
| 6,451,300 B1 | 9/2002 | Dunlop et al. | |
| 6,521,238 B1 | 2/2003 | Muller | |
| 6,521,239 B1 | 2/2003 | Breton | |
| RE38,130 E | 6/2003 | Adams | |
| 6,616,325 B1 * | 9/2003 | Brown | B01F 25/60 366/302 |
| 6,719,967 B1 | 4/2004 | Brown | |
| 6,774,096 B1 | 8/2004 | Paye | |
| 6,878,368 B2 | 4/2005 | Ohta et al. | |
| 6,908,912 B2 | 6/2005 | Rioux | |
| 6,991,799 B2 | 1/2006 | Pham et al. | |
| 7,294,611 B2 | 11/2007 | Metrot | |
| 7,303,744 B2 | 12/2007 | Wells | |
| 7,531,497 B2 | 5/2009 | Midha et al. | |
| 7,560,125 B2 | 7/2009 | Ananthapadmanabhan et al. | |
| 7,776,347 B2 | 8/2010 | Kerschner et al. | |
| 8,252,271 B2 | 8/2012 | Singer et al. | |
| 8,349,300 B2 | 1/2013 | Wells | |
| 8,349,301 B2 | 1/2013 | Wells et al. | |
| 8,349,302 B2 | 1/2013 | Johnson et al. | |
| 8,361,448 B2 | 1/2013 | Johnson et al. | |
| 8,361,449 B2 | 1/2013 | Wells et al. | |
| 8,361,450 B2 | 1/2013 | Johnson et al. | |
| 8,367,048 B2 | 2/2013 | Wells et al. | |
| 8,470,305 B2 | 6/2013 | Johnson et al. | |
| 8,635,014 B2 | 1/2014 | Jung | |
| 8,653,014 B2 | 2/2014 | Hilvert et al. | |
| 8,655,819 B1 | 2/2014 | Burkard et al. | |
| 8,663,612 B2 | 3/2014 | Gamez-Garcia et al. | |
| 8,901,062 B2 | 12/2014 | De Meirleir et al. | |
| 8,932,569 B2 | 1/2015 | Garrison et al. | |
| 8,940,285 B2 | 1/2015 | Leray et al. | |
| 8,969,261 B2 | 3/2015 | Talingting Pabalan et al. | |
| 9,005,585 B2 | 4/2015 | Deckner et al. | |
| 9,138,429 B2 | 9/2015 | Wise et al. | |
| 9,381,382 B2 | 7/2016 | Schwartz et al. | |
| 9,393,188 B2 | 7/2016 | Deckner et al. | |
| 9,539,444 B2 | 1/2017 | Kinoshita | |
| 9,587,209 B2 | 3/2017 | De Meirleir et al. | |
| 9,724,283 B2 | 8/2017 | Rizk | |
| 9,877,909 B2 | 1/2018 | Cetti et al. | |
| 10,143,632 B2 | 12/2018 | Dihora et al. | |
| 10,226,782 B2 | 3/2019 | Yamaguchi et al. | |
| 10,689,183 B2 | 6/2020 | Moretti | |
| 10,912,719 B2 | 2/2021 | Gulbin | |
| 10,945,935 B2 | 3/2021 | Brown et al. | |
| 2001/0047039 A1 | 11/2001 | Mcmanus | |
| 2002/0119113 A1 | 8/2002 | Ellis | |
| 2002/0131946 A1 | 9/2002 | Pham et al. | |
| 2002/0169283 A1 | 11/2002 | Lu | |
| 2002/0183300 A1 | 12/2002 | Fliss | |
| 2003/0012646 A1 | 1/2003 | Liao | |
| 2003/0017126 A1 | 1/2003 | Mahadeshwar | |
| 2003/0044471 A1 | 3/2003 | Sakuma | |
| 2003/0095938 A1 | 5/2003 | Casero | |
| 2003/0119806 A1 | 6/2003 | Lindell | |
| 2003/0130145 A1 | 7/2003 | Patel | |
| 2003/0138497 A1 | 7/2003 | Sakuma | |
| 2003/0171231 A1 | 9/2003 | Shana | |
| 2003/0185779 A1 | 10/2003 | Mitsumatsu | |
| 2003/0215522 A1 | 11/2003 | Johnson | |
| 2003/0223952 A1 | 12/2003 | Wells et al. | |
| 2003/0224954 A1 | 12/2003 | Wells et al. | |
| 2003/0224955 A1 | 12/2003 | Ribery | |
| 2004/0058855 A1 | 3/2004 | Schwartz | |
| 2004/0092897 A1 | 5/2004 | Macedo, Jr. | |
| 2004/0157754 A1 | 8/2004 | Geary et al. | |
| 2004/0167114 A1 | 8/2004 | Fliss | |
| 2004/0191331 A1 | 9/2004 | Schwartz | |
| 2004/0197294 A1 | 10/2004 | Seipel | |
| 2004/0223941 A1 | 11/2004 | Schwartz | |
| 2004/0223991 A1 * | 11/2004 | Wei | A61Q 19/00 424/401 |
| 2004/0234471 A1 | 11/2004 | Corbella | |
| 2004/0266886 A1 | 12/2004 | Seipel | |
| 2005/0031569 A1 | 2/2005 | Seipel | |
| 2005/0100570 A1 | 5/2005 | Wei et al. | |
| 2005/0112083 A1 | 5/2005 | Wells et al. | |
| 2005/0143268 A1 | 6/2005 | Midha | |
| 2005/0181067 A1 | 8/2005 | Yokoyama | |
| 2005/0196368 A1 | 9/2005 | Laurent et al. | |
| 2005/0202984 A1 | 9/2005 | Schwartz | |
| 2005/0267258 A1 | 12/2005 | Rajaraman et al. | |
| 2006/0024256 A1 | 2/2006 | Wells | |
| 2006/0024381 A1 | 2/2006 | Schwartz | |
| 2006/0025256 A1 | 2/2006 | Wake | |
| 2006/0045861 A1 | 3/2006 | Bejger | |
| 2006/0078524 A1 | 4/2006 | Midha et al. | |
| 2006/0078527 A1 | 4/2006 | Midha et al. | |
| 2006/0079418 A1 | 4/2006 | Wagner et al. | |
| 2006/0079419 A1 | 4/2006 | Wagner et al. | |
| 2006/0079420 A1 | 4/2006 | Wagner et al. | |
| 2006/0079421 A1 | 4/2006 | Wagner et al. | |
| 2006/0205631 A1 | 9/2006 | Smerznak et al. | |
| 2006/0250658 A1 | 11/2006 | Jurgensen | |
| 2006/0251605 A1 | 11/2006 | Belmar | |
| 2006/0269501 A1 | 11/2006 | Johnson | |
| 2006/0269502 A1 | 11/2006 | Johnson | |
| 2007/0095721 A1 | 5/2007 | Davis et al. | |
| 2007/0110696 A1 | 5/2007 | Johnson | |
| 2007/0110700 A1 | 5/2007 | Wells | |
| 2007/0128147 A1 | 6/2007 | Schwartz et al. | |
| 2007/0280976 A1 | 12/2007 | Taylor et al. | |
| 2008/0039352 A1 | 2/2008 | Wells et al. | |
| 2008/0096786 A1 | 4/2008 | Holt et al. | |
| 2008/0152611 A1 | 6/2008 | Wells | |
| 2008/0187507 A1 | 8/2008 | Johnson | |
| 2010/0061952 A1 | 3/2010 | Wells et al. | |
| 2010/0226868 A1 | 9/2010 | Gamez-Garcia et al. | |
| 2010/0234260 A1 | 9/2010 | Sekine et al. | |
| 2010/0322878 A1 | 12/2010 | Stella et al. | |
| 2010/0330018 A1 | 12/2010 | Lorant et al. | |
| 2011/0053818 A1 | 3/2011 | Chuchotiros et al. | |
| 2011/0065624 A1 | 3/2011 | Boutique | |
| 2011/0067720 A1 | 3/2011 | Ranade et al. | |
| 2011/0070180 A1 | 3/2011 | Ranade et al. | |
| 2011/0081392 A1 | 4/2011 | de Arruda et al. | |
| 2011/0110991 A1 | 5/2011 | Garrison et al. | |
| 2011/0248052 A1 | 10/2011 | Kelly et al. | |
| 2012/0148644 A1 | 6/2012 | Popplewell et al. | |
| 2012/0164198 A1 | 6/2012 | Johnson et al. | |
| 2012/0308502 A1 | 12/2012 | Wise et al. | |
| 2012/0329768 A1 | 12/2012 | Wise et al. | |
| 2013/0029894 A1 | 1/2013 | Bettiol et al. | |
| 2013/0090279 A1 | 4/2013 | Hilvert et al. | |
| 2013/0131188 A1 | 5/2013 | Beckedahl et al. | |
| 2013/0143784 A1 | 6/2013 | Rizk | |
| 2013/0171216 A1 | 7/2013 | Alden-danforth et al. | |
| 2013/0174863 A1 | 7/2013 | Marsh et al. | |
| 2013/0243717 A1 | 9/2013 | Catalan et al. | |
| 2013/0243835 A1 | 9/2013 | Tanner et al. | |
| 2014/0018276 A1 | 1/2014 | Coffindaffer et al. | |

(56) References Cited

U.S. PATENT DOCUMENTS

| | | |
|---|---|---|
| 2014/0099276 A1 | 4/2014 | Yang et al. |
| 2014/0112964 A1 | 4/2014 | Wu |
| 2014/0162931 A1 | 6/2014 | De Meirleir et al. |
| 2014/0335041 A1 | 11/2014 | Peffly et al. |
| 2015/0010487 A1 | 1/2015 | Snyder et al. |
| 2015/0011450 A1 | 1/2015 | Carter et al. |
| 2015/0044157 A1 | 2/2015 | Kulkarni et al. |
| 2015/0093422 A1 | 4/2015 | Garrison et al. |
| 2015/0102061 A1 | 4/2015 | Larson et al. |
| 2015/0313833 A1 | 11/2015 | Hilvert et al. |
| 2015/0342842 A1 | 12/2015 | Wise et al. |
| 2015/0374609 A1* | 12/2015 | Cetti ............... B65B 63/08 53/440 |
| 2016/0106663 A1 | 4/2016 | Gulbin |
| 2016/0143827 A1 | 5/2016 | Castan Barberan et al. |
| 2016/0256365 A1 | 9/2016 | Dihora et al. |
| 2017/0102720 A1* | 4/2017 | Goudy ............... F16K 3/0218 |
| 2017/0216158 A1 | 8/2017 | Deckner et al. |
| 2017/0225183 A1 | 8/2017 | Kelly |
| 2017/0333734 A1 | 11/2017 | Mauer et al. |
| 2017/0367955 A1 | 12/2017 | Brown et al. |
| 2018/0071185 A1 | 3/2018 | Cochran et al. |
| 2018/0098923 A1 | 4/2018 | Hutton, III |
| 2018/0339845 A1 | 11/2018 | Moretti |
| 2018/0354767 A1* | 12/2018 | Cacciatore ............... B67C 3/24 |
| 2018/0354769 A1* | 12/2018 | Cacciatore ............... B67C 3/02 |
| 2018/0354770 A1* | 12/2018 | Cacciatore ............ B67C 3/208 |
| 2019/0105246 A1 | 4/2019 | Cochran et al. |
| 2019/0105247 A1 | 4/2019 | Song et al. |
| 2019/0201925 A1 | 7/2019 | Toh et al. |
| 2019/0290554 A1 | 9/2019 | Yokogi et al. |
| 2019/0290555 A1 | 9/2019 | Yokogi et al. |
| 2019/0290562 A1 | 9/2019 | Yokogi et al. |
| 2019/0290567 A1 | 9/2019 | Yokogi et al. |
| 2019/0290568 A1 | 9/2019 | Yokogi et al. |
| 2019/0307665 A1 | 10/2019 | Yokogi et al. |
| 2019/0365611 A1 | 12/2019 | Brown et al. |
| 2020/0188243 A1* | 6/2020 | Brown ............... A61K 8/0254 |
| 2021/0022975 A1 | 1/2021 | Cochran et al. |
| 2021/0045979 A1* | 2/2021 | Dunlop ............... A61K 8/602 |
| 2021/0253303 A1 | 8/2021 | Bartolucci et al. |

FOREIGN PATENT DOCUMENTS

| | | |
|---|---|---|
| CN | 1213294 A | 4/1999 |
| CN | 1568174 A | 1/2005 |
| CN | 1658825 A | 8/2005 |
| CN | 1658830 A | 8/2005 |
| CN | 101267797 A | 9/2008 |
| CN | 101965175 A | 2/2011 |
| CN | 102905682 A | 1/2013 |
| CN | 103458858 A | 12/2013 |
| CN | 105326660 A | 2/2016 |
| CN | 105326670 A | 2/2016 |
| CN | 105395373 A | 3/2016 |
| CN | 105326660 B | 4/2018 |
| CN | 105395378 B | 7/2018 |
| DE | 19847968 A1 | 4/2000 |
| EP | 0037318 A1 | 10/1981 |
| EP | 0077630 A1 | 4/1983 |
| EP | 0627216 A2 | 12/1994 |
| EP | 1123693 A2 | 8/2001 |
| EP | 1066024 B1 | 10/2002 |
| EP | 1384467 B1 | 5/2007 |
| EP | 3075681 A1 | 10/2016 |
| FR | 2544890 A1 * | 10/1984 |
| FR | 2593801 B1 | 5/1986 |
| FR | 1971709 A1 | 8/2012 |
| FR | 2984136 A1 | 6/2013 |
| GB | 849433 A1 | 9/1960 |
| GB | 1582529 A | 1/1981 |
| GB | 2177108 B | 7/1989 |
| JP | 5209881 A | 8/1977 |
| JP | 06134227 A | 5/1994 |
| JP | H07179887 A | 11/1994 |
| JP | H07118103 A | 5/1995 |
| JP | 07258039 A | 10/1995 |
| JP | 2001181145 A | 7/2001 |
| JP | 2002104940 A | 4/2002 |
| JP | 2003530446 A | 10/2003 |
| JP | 2004262805 A | 9/2004 |
| JP | 2004292387 A | 10/2004 |
| JP | 2004292390 A | 10/2004 |
| JP | 2004307463 A | 11/2004 |
| JP | 2005022983 A | 1/2005 |
| JP | 2005187342 A | 7/2005 |
| JP | 2006063044 A | 3/2006 |
| JP | 2006525232 A | 11/2006 |
| JP | 4016238 B2 | 9/2007 |
| JP | 2007527921 A | 10/2007 |
| JP | 4069228 B2 | 1/2008 |
| JP | 4129645 B2 | 5/2008 |
| JP | 2008524263 A | 7/2008 |
| JP | 2015512248 A | 4/2015 |
| JP | 2016516674 A | 6/2016 |
| WO | 9308787 A1 | 5/1993 |
| WO | 9410973 A1 | 5/1994 |
| WO | 9625913 A1 | 8/1996 |
| WO | 9726854 A1 | 7/1997 |
| WO | 9847372 A1 | 10/1998 |
| WO | 9938489 A1 | 8/1999 |
| WO | 9959540 A1 | 11/1999 |
| WO | 0100149 A1 | 1/2001 |
| WO | 0105932 A1 | 1/2001 |
| WO | 0117492 A1 | 3/2001 |
| WO | 0119946 A1 | 3/2001 |
| WO | 0139735 A1 | 6/2001 |
| WO | 02060995 A2 | 8/2002 |
| WO | 02076422 A1 | 10/2002 |
| WO | 2004020526 A1 | 3/2004 |
| WO | 2004100919 A1 | 11/2004 |
| WO | 2009072027 A2 | 6/2009 |
| WO | 2009074465 A2 | 6/2009 |
| WO | 2010006866 A1 | 1/2010 |
| WO | 2010034736 A1 | 4/2010 |
| WO | 2010111266 A2 | 9/2010 |
| WO | 2011120799 A1 | 10/2011 |
| WO | 2011134832 A2 | 11/2011 |
| WO | 2012004126 A2 | 1/2012 |
| WO | 2012138696 A2 | 10/2012 |
| WO | 2012175677 A2 | 12/2012 |
| WO | 20121756821 A2 | 12/2012 |
| WO | 2013073849 A1 | 5/2013 |
| WO | 2016040158 A1 | 3/2016 |
| WO | 2017088459 A1 | 6/2017 |
| WO | 2018005453 A1 | 1/2018 |
| WO | 2019236646 A1 | 12/2019 |
| WO | WO-2020264569 A1 * | 12/2020 ............ A61K 8/042 |
| WO | 2021163728 A1 | 8/2021 |

OTHER PUBLICATIONS

All Office Actions; U.S. Appl. No. 17/174,713, filed Feb. 12, 2021.
U.S. Appl. No. 17/184,814, filed Feb. 25, 2021, to Mark Anthony Brown et al.
U.S. Appl. No. 17/174,713, filed Feb. 12, 2021, to Mark Anthony Brown et al.
De Meirleir et al. "Journal of Crystal Growth" 2013; 383: 51-56. (Year: 2013).
"Herbal Essence Shampoo", Mintel, Jun. 1, 2014, 2 pages.
"Polyelectrolyte-Micelle—Coacervation—Effect of coacervate on the properties of shampoo", Yoshiko Kiwatari et al., J. Soc. Cosmet. Chem. Japan, vol. 38, No. 3, 2004, pp. 211-219.
Eccleston, G.M., Application of Emulsion Stability Theories to Mobile and Semisolid o/w Emulsions, Cosmetics Magazine, vol. 101, 1986, 18 pages.
International Search Report and Written Opinion; Application Ser. No. PCT/US2020/070185 dated Oct. 30, 2020, 11 pages.
PCT Search Report and Written Opinion for PCT/US2021/070145 dated Jun. 2, 2021, 11 pages.

(56) References Cited

OTHER PUBLICATIONS

Eccleston, G.M., Application of Emulsion Theory to Complex and Real Systems, International Journal of Cosmetic Science, 1985, 18 pages.
Eccleston, G.M., Formulating Cosmetic Emulsions, Cosmetics Magazine, vol. 112, 1997, 2 pages.
Eccleston, G.M., Functions of Mixed Emulsifiers and Emulsifying Waxes in Dermatological Lotions and Creams, Colloids and Surfaces, vol. 123, 1997, 14 pages.
Eccleston, G.M., Microstructural Changes During Storage of Cetostearyl Alcohol/ Polyoxyethylene Alkyl Ether Surfactants, University of Strathclyde, 1988, 20 pages.
Eccleston, G.M., Multiple Phase Oil and Water Emulsions, Journal of Cosmetic Chemists, 1990, 22 pages.
Eccleston, G.M., Structure and Rheology of Semisolid o/w Creams Containing Cetyl Alcohol/Non-ionic Surfactant Mixed Emulsifier and Different Polymers, International Journal of Cosmetic Science, 2004, 7 pages.
Eccleston, G.M., Synchrotron X-ray Investigations into the Lamellar Gel Phase Formed in Creams Prepared with Fatty Alcohols, International Journal of Pharmaceuticals, 2000, 13 pages.
Eccleston, G.M., The Influence of Fatty Alcohols on the Structure and Stability of Creams Preapred with Fatty Alcohols, International Journal of Cosmetic Science, 1982, 9 pages.
All Office Actions, U.S. Appl. No. 15/635,633.
All Office Actions, U.S. Appl. No. 15/703,046.
All Office Actions, U.S. Appl. No. 15/728,663.
All Office Actions, U.S. Appl. No. 16/713,142.
All Office Actions, U.S. Appl. No. 16/902,629.
All Office Actions, U.S. Appl. No. 16/432,371.
All Office Actions, U.S. Appl. No. 17/174,427.
All Office Actions, U.S. Appl. No. 17/326,910.
All Office Actions, U.S. Appl. No. 17/327,972.
Barry & Rowe, The Characterization by Small Angle X-Ray Scattering of a Gel with a Lamellar Structure, International Journal of Pharmaceuticals, 1989, 2 pages.
Barry & Saunders, Kinetics of Structure Build-up in Self Bodied Emulsions Stabalized by Mixed Emulsifiers, Journal of Colloid Science, vol. 41, 1972, 12 pages.
Barry, B.W., Structure and Rheology of Emulsions Stabalized by Mixed Emulsifiers, British Society of Rheology, 1970, 12 pages.
Benton et al, Phase Behavior and Network Formation in a Cationic Surfactant-Fatty Alcohol System, JAOCS, vol. 64, 1987, 12 pages.
Burgess, J.D., Practical Analysis of Complex Coacervate Systems, Journal of Colloid Science, vol. 140, 1990, 10 pages.
CTFA Cosmetic Ingredient Dictionary, 1982, 3rd Edition, The Cosmetic, Toiletry & Fragrance Association, Inc., Washington, DC (book not included).
Database WPI Week 201634Thomson Scientific, London, GB;AN 2016-184949XP002798128,& CN 105 395 373 A (Cuongqing Pellets Coltd) Mar. 16, 2016 (Mar. 16, 2016)abstract, 3 pages.
Database WPI Week 201644Thomson Scientific, London, GB;AN 2016-14284BXP002798127,& CN 105 326 660 A (Chongqing Pellets Colid) Feb. 17, 2016 (Feb. 17, 2016)abstract, 3 pages.

Encyclopedia of Polymer Science and Engineering, John Wiley & Sons, vol. 15, 1989 (book not included).
Griffin, W.C., Calculation of HLB Values of Non-Ionic Surfactants, Journal of the Society of Cosmetic Chemists; 1954. vol. 5, pp. 249-235.
Korhonen et al, Rheological Properties of Three Component Creams Containing Sorbitan Monoesters as Surfactants, International Journal of Pharmaceuticals, 2002, 2 pages.
Louden et al, A Preliminary Examination of the Structure of Gels and Emulsions Containing Cetostearyl Alcohol, International Journal of Pharmaceuticals, 1985, 2 pages.
McCutcheon, Emulsifiers and Detergents, MC Pub Company, 1989 (book not included).
Meirleir Niels De et al., "The rheological properties of hydrogenated castor oil crystals", Colloid & Polymer Science, Springer Verlag, Heidelberg, DE, vol. 292, No. 10, Jun. 12, 2014, pp. 2539-2547.
Momentive SFE839 product brochure, https://www.momentive.com/products/showtechnicaldatasheet.aspx?id=14443, 4 pagesavailable Sep. 2008; accessed Jul. 17, 2015.
Noll, W., Chemistry and Technology of Silicones, Academic Press, 1968 (book not included).
Patel et al, Properties of Cetrimide / Cetostearyl Alcohol Ternary Gels; Preparation Effects, International Journal of Pharmaceuticals, 1985, 2 pages.
Savic et al, Colloidal Microstructure of Binary Systems and Model Creams Stablized with an Alkylpolyglucoside Emulsifier, Colloid Polymer Science, vol. 283, 2004, 13 pages.
Saxton, C., Antiplaque Effects and Mode of Action of a Combination of Zinc Citrate and a Nonionic Antimicrobial Agent, Scandinavian Journal, vol. 96, 1988, 7 pages.
Suzuki et al, Secondary Droplet Emulsion: Mechanism & Effects of Liquid Crystal Formation in o/w Emulsion, Journal of Dispersion Science, 1984, 24 pages.
U.S. Appl. No. 17/174,427, filed Feb. 12, 2021, to Stefano Bartolucci et al.
U.S. Appl. No. 17/326,910, filed May 21, 2021, to Howard David Hutton.
U.S. Appl. No. 17/327,972, filed May 24, 2021, to Howard David Hutton.
Van Cutsem, Journal of the American Academy of Dermatology, XP-002288119, 1998, 2 pages.
Van Oss, C.J., Coacervation, Complex Coacervation and Flocculation, Journal of Dispersion Science, vol. 9, 1989, 14 pages.
Yoon et al, A Study of Gel Structure in the Nonionic Surfactant / Cetostearyl Alcohol / Water Ternary Systems by Differential Scanning Calorimeter, Journal of Dispersion Science, 1999, 20 pages.
All Office Actions; U.S. Appl. No. 18/174,082, filed Feb. 24, 2023.
U.S. Appl. No. 18/174,082, filed Feb. 24, 2023 to Mark Anthony Brown et al.
"INCI: Ricinus Communis (Castor) Seed Oil", Caschem, No Known date, 3 pages.

* cited by examiner

 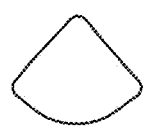 
Fig. 5a    Fig. 5b    Fig. 5c
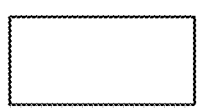  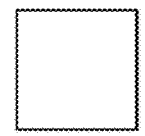
Fig. 5d    Fig. 5e    Fig. 5f
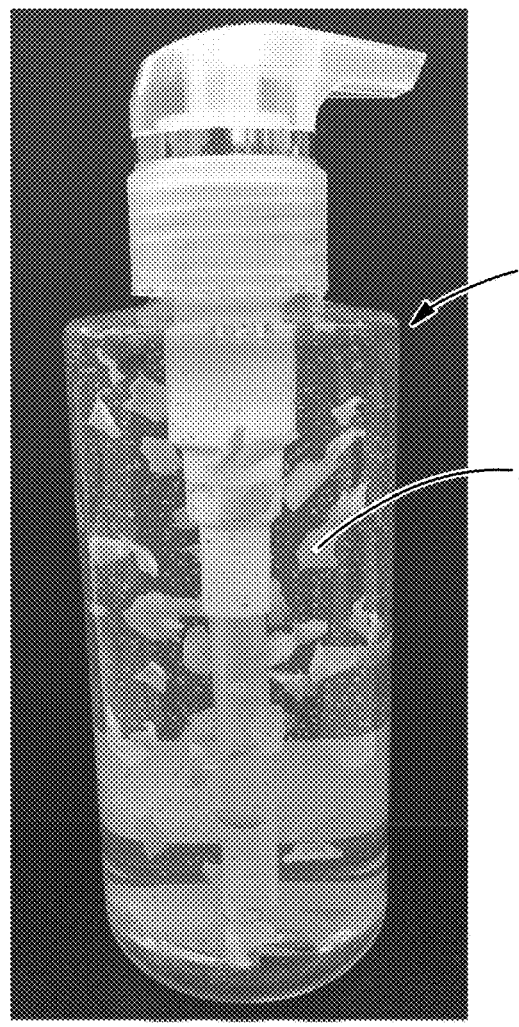
Fig. 6

METHOD OF MAKING A CLEAR PERSONAL CARE COMPRISING MICROCAPSULES

FIELD OF THE INVENTION

The present disclosure generally relates to methods of making personal care compositions which include microcapsules.

BACKGROUND OF THE INVENTION

Consumers desire a product which delivers both good in use benefits, and also has an aesthetically pleasing product appearance. It can be difficult to incorporate aesthetic materials like microcapsules, without breaking or damaging the microcapsules, thereby ruining the aesthetic appearance of the product. The microcapsules may roll up or fold over when being incorporated into the product. Additionally, when adding microcapsules to a personal care composition, often air is also introduced into the method of manufacturing. The air bubbles that form can make the product appear opaque rather than clear, which detracts from the aesthetic appearance of the microcapsules, as the air bubbles can mask the presence of the microcapsules. While low levels of air may be useful for aesthetics, higher levels contribute to the opaque appearance described above. And, without a strategy to control the amount of air bubbles added, it is difficult to get a consistent appearance bottle to bottle in a manufacturing process.

It has been surprisingly found that using the disclosed method results in personal care products containing microcapsules which delivers an aesthetically pleasing product appearance in bottle.

SUMMARY OF THE INVENTION

The invention relates to a method of making a personal care composition, the method comprising steps of: providing a mixer comprising a housing comprising a first fluid inlet, a second inlet, and a fluid outlet, the mixer further rotor rotatably connected with the housing, the rotor comprising blades positioned within the housing to define cells between neighboring blades and the housing; preparing a personal care chassis base comprising surfactants and water; preparing a microcapsule composition comprising microcapsules, and air; advancing personal care chassis base along a flow path from the first fluid inlet toward the fluid outlet; transferring the microcapsule composition from the second inlet to the flow path by rotating the rotor; directing air in the microcapsule composition from inside the cells toward the second inlet; combining the microcapsule composition with the personal care chassis base to form the personal care composition; and advancing the personal care composition from the outlet. The microcapsule composition may further comprise an aqueous carrier including, but not limited to, water. The personal care composition may be conveyed to a filling nozzle.

BRIEF DESCRIPTION OF THE DRAWINGS

FIGS. 5A-5F are shaped microcapsule.

FIG. 6 is a photograph of a shampoo product comprising a petal shaped sheet-like microcapsule.

DETAILED DESCRIPTION OF THE INVENTION

Figure 1:
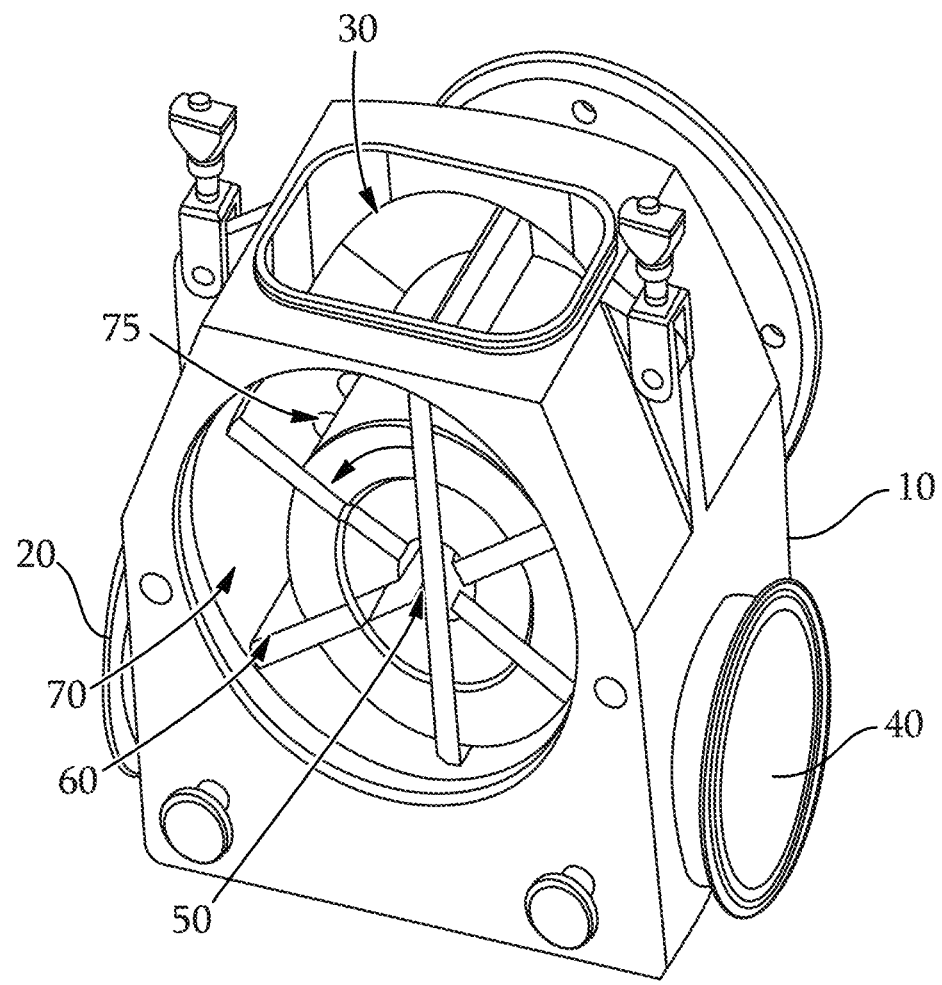
FIG. 1 shows a perspective view of the arrangement for the mixing of the microcapsules into the personal care chassis.

While the specification concludes with claims particularly pointing out and distinctly claiming the invention, it is believed that the present disclosure will be better understood from the following description.

As used herein, the term "fluid" includes liquids and gels.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "M.Wt." refers to the weight average molecular weight unless otherwise stated. Molecular weight is measured using industry standard method, gel permeation chromatography ("GPC"). The molecular weight has units of grams/mol.

As used herein, "personal care composition" includes personal care products such as shampoos, body wash, face wash, shampoo conditioners, conditioning shampoos, and other surfactant-based liquid compositions.

As used herein, the terms "include," "includes," and "including," are meant to be non-limiting and are understood to mean "comprise," "comprises," and "comprising," respectively.

All percentages, parts and ratios are based upon the total weight of the compositions described herein, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

A. Method

The personal care compositions can be made by forming a personal 5 care chassis by 1) adding water and surfactants, 2) add thickeners, stabilizing agents (optional) like EGDS, Trihydroxystearin, acrylate thickening polymers, etc., 3) adding conditioning agents (optional) like polymers, silicones, oils, etc., and 4) add aesthetic agents like perfume, color (optional) and preservative agents. These materials can be combined together via conventional means. Typically, 10 the above steps introduce enough air bubbles into the product to make the finished personal care product opaque. The opaque appearance can be the result of too many visible air bubbles. The air is introduced by mixing as well as when the microcapsules are added, air surrounds these materials and it is blended into personal care composition. If the product will stabilize solid particulates (e.g. microcapsules) it will also stabilize air of a given size and as a result the air bubbles will not leave 15 the product and it will tend to look opaque over time. It is possible that over long periods of time air bubbles may slowly disappear through a variety of mechanisms such as bubbles rising if yield stress is not sufficient for a given bubble size, changes in air solubility in the fluid from temperature changes, and diffusion/ripening. These mechanisms, while sometimes giving products that have no visible air bubbles eventually, can require many weeks or months or perhaps years to effectively leave the product without air bubbles. It is not desired to have air bubbles persisting in the fluid since consumer will purchase the product before the air bubbles have predictably left the fluid. Therefore, it is desired to form a product with a low amount of air so that the product on shelf has a predictable amount of visible microcapsules. An acceptable level of bubbles in the personal care composition can be tested multiple ways, including but not limited to using the L* test described herein, wherein the personal care composition has a L* value of from 0 to about 40. Alternatively the personal care composition having an acceptable bubble impact to appearance can be determined using the Visual Opaque Evaluation method described herein.

A method of making a clear personal care composition (absent opaqueness resulting from air bubbles) includes first providing a mixer (FIG. 1) comprising a housing 10 comprising a first fluid inlet 20, a second inlet 30, and a fluid outlet 40, the mixer further rotor rotatably connected 50 with the housing 10, the rotor comprising blades 60 positioned within the housing to define cells 70 between neighboring blades and the housing. Prepare a personal care chassis base comprising surfactant(s), aqueous carrier, optionally thickeners, polymers, conditioning agents, perfumes, and preservative agents and preparing a microcapsule composition comprising microcapsules. The microcapsules composition may enter the system with air. The air is introduced to this system as air which naturally surrounds the microcapsules. Alternatively, a liquid/slurry premix with the microcapsules and an aqueous carrier can be formed and this liquid/slurry pumped in a continuous fashion to the vane pump portion of the ingredient doser. This liquid/slurry can be surrounded by air as it enters the second inlet (FIG. 1, at 30). The personal care chassis advances at a rate of from about 1.5 L/min to about 200 L/min; alternatively from about 50 L/min to about 150 L/min.

Figure 2:
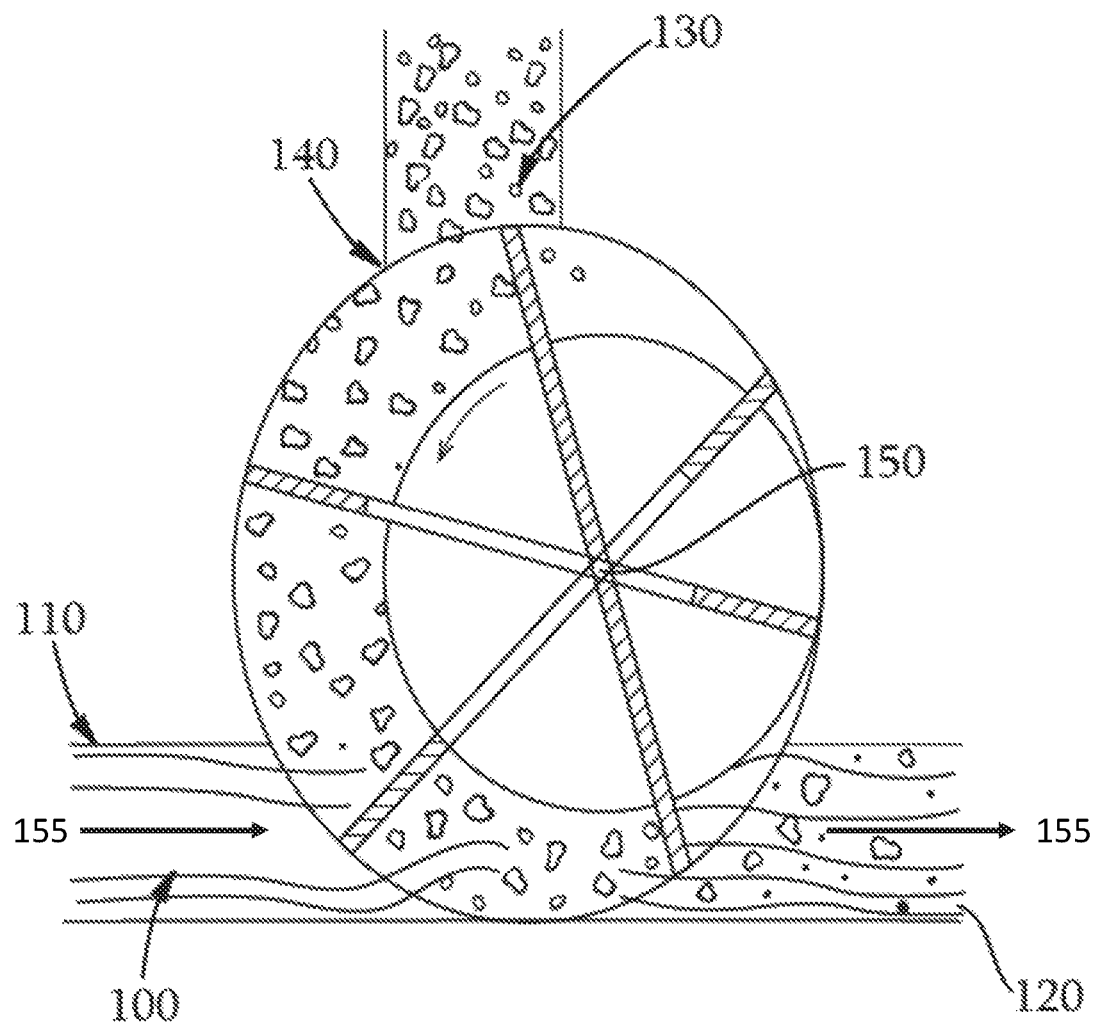
FIG. 2 shows a longitudinal section through the middle part of the arrangement of FIG. 1.
Figure 3A:
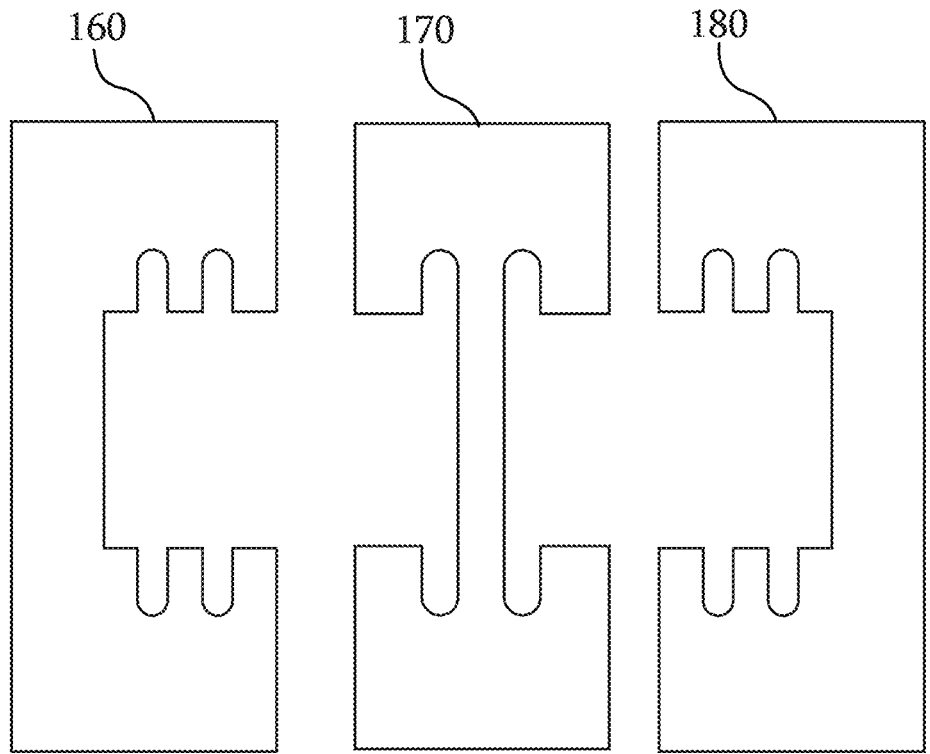
FIG. 3A shows examples of a set of rotor blades for the arrangement's rotor.
Figure 3B:
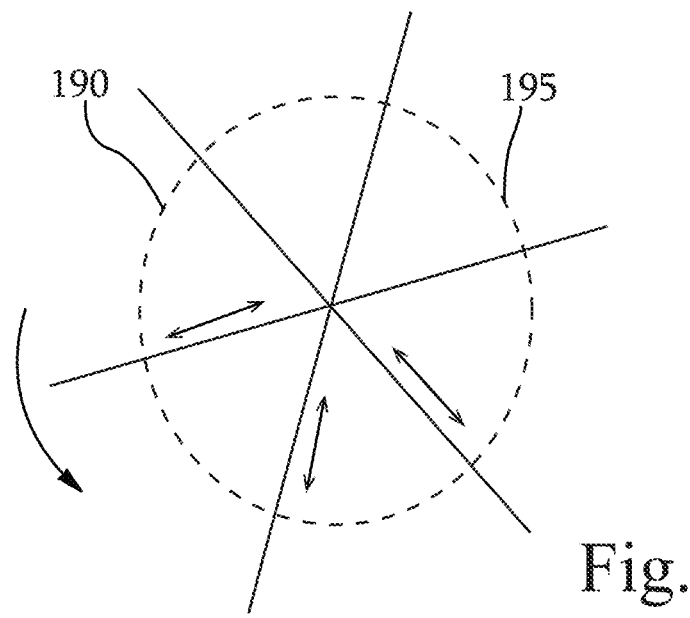
FIG. 3B shows a set of rotor blades from 3A together in the form of the arrangement's rotor.
Figure 4A:
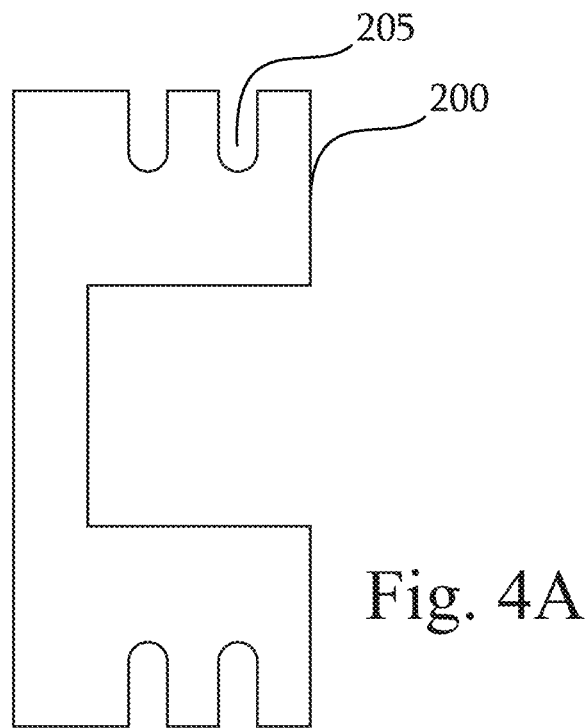
FIG. 4A and 4B shows two alternative rotor blades suitable for use in the arrangement.
Figure 4B:
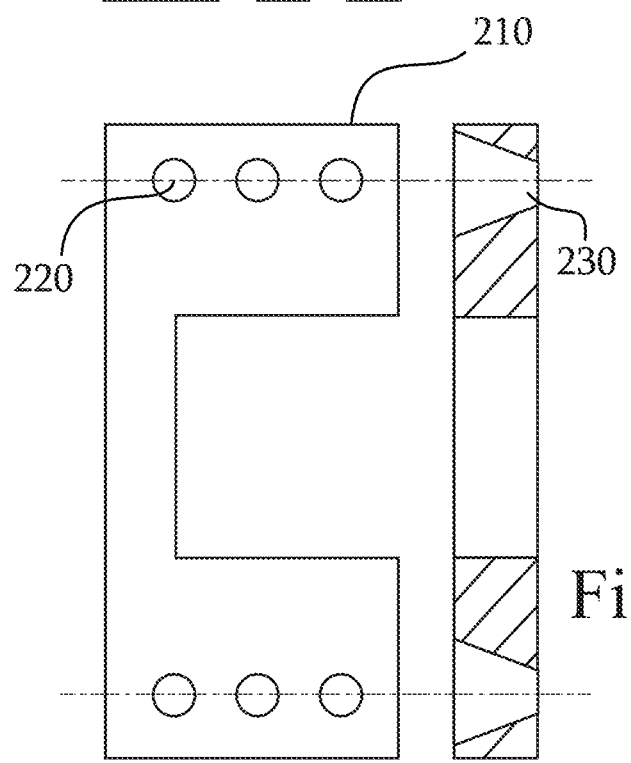

As shown in FIG. 2 advance the personal care chassis base 100 along a flow path 155 from the first fluid inlet 110 toward the fluid outlet 120, and then transfer the microcapsule composition 130 through the second inlet 140 to the flow path 155 by rotating the rotor 150. Air can also enter the system as the rotor 150 incorporates the microcapsule composition 130. Then air is removed from the process by directing air in the microcapsule composition 130 from inside the cells toward the second inlet 140. The air can escape via apertures in the rotor blades (FIG. 1 at 75), and/or forcing the air through gaps between the rotor blades and the mixer housing. In addition, the apertures can be straight through the rotor blades in a perpendicular direction to the long axis of the rotor blades or the apertures can be angled so as to direct the flow of venting air and liquid to one side of the rotor housing. The apertures can be any shape or size, suitable shapes include round, rectangular, oval etc. Suitable sizes include from about 0.1 mm to about 10 mm, from about 0.5 mm to 5 mm, from about 1 mm to about 3 mm. In addition, the apertures can be designed so they expand or contract through the rotor blades so one side of the rotor blade may have a smaller hole than the other side as the aperture expands as it progresses through the rotor blade. Next combine the microcapsule composition 130 with the personal care chassis base 100 to form the personal care composition; and advance the personal care composition from the outlet 120. FIG. 3A shows examples of a set of rotor blades for the arrangement's rotor 160, 170, 180, and the rotor 195. FIG. 3B shows a set of rotor blades from 3A together in the form of the arrangement's rotor 190; FIG. 4A shows a rotor blade 200 with apertures 205 and 4B shows a rotor blade 210 with an aperture 220, 230 suitable for use in the arrangement.

The personal care composition exiting the fluid outlet (FIG. 1, 40) is then blended to uniformly distribute the microcapsules in the personal care composition. The blended personal care composition is then conveyed to the filling line. Optimally, this is a short distance from the ingredient doser. An optional surge tank can also be used between the filler and the ingredient doser to provide a buffer to enable the ingredient doser to keep running for periods of time when the filler stops operating. Alternatively, the method does not use any storage tanks and runs as a continuous process.

Figure 7:
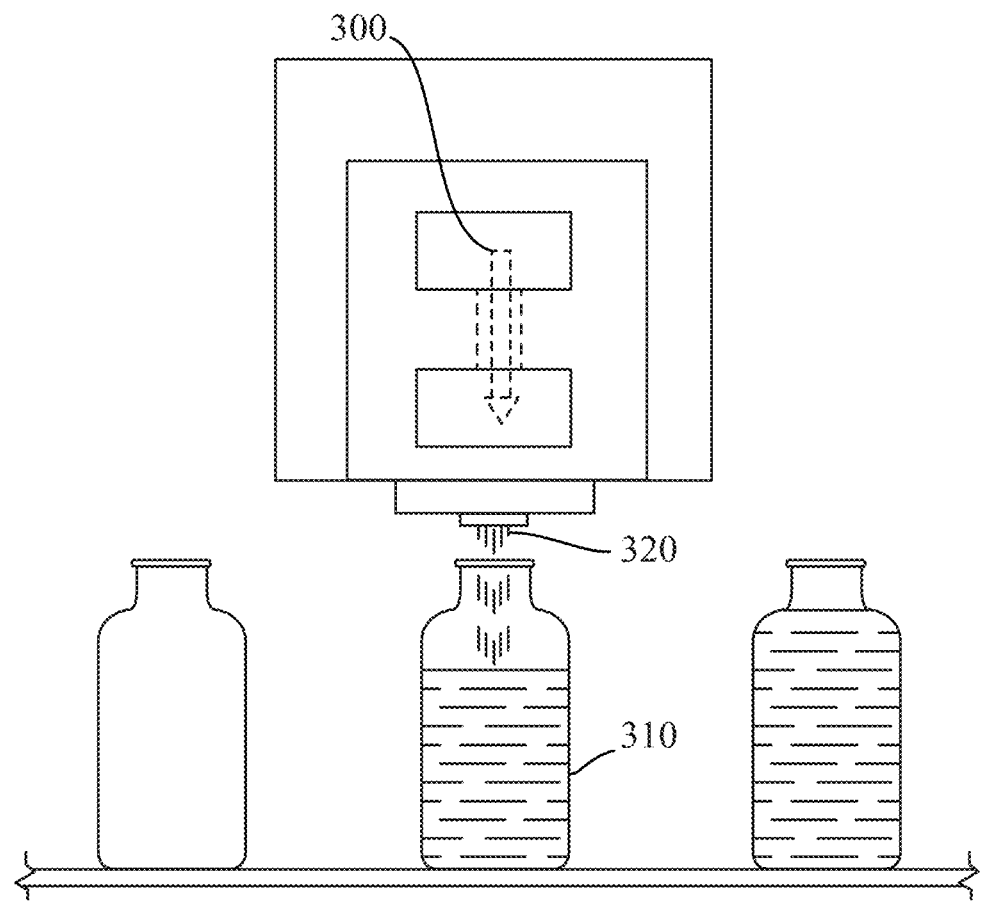
FIG. 7 is a perspective view of one exemplary embodiment of the shutoff valve assembly of the present invention in a bottle filling assembly line.
Figure 8:
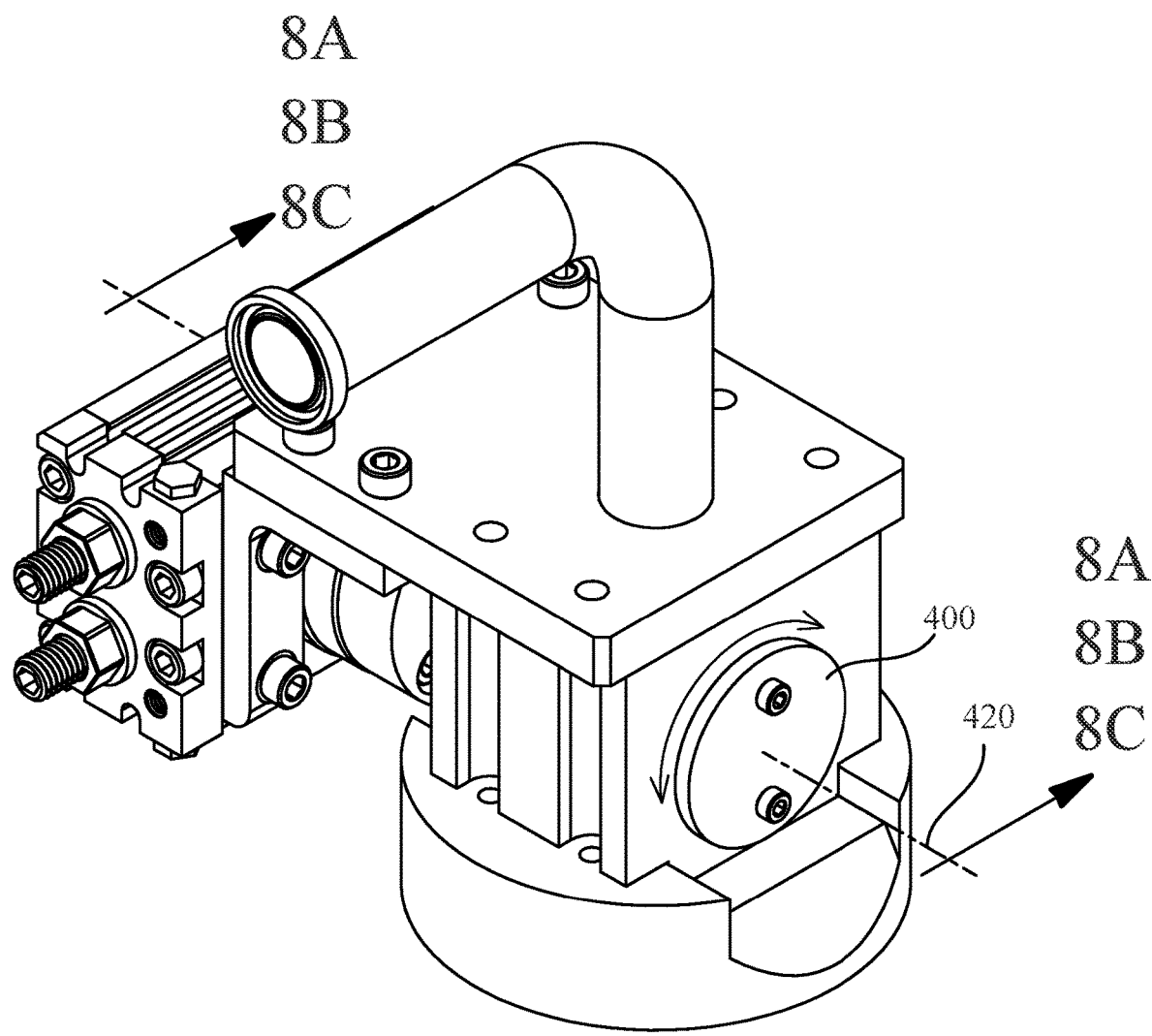
FIGS. 8 is a view of one exemplary embodiment of the shutoff valve assembly of the present invention.
Figure 8A:
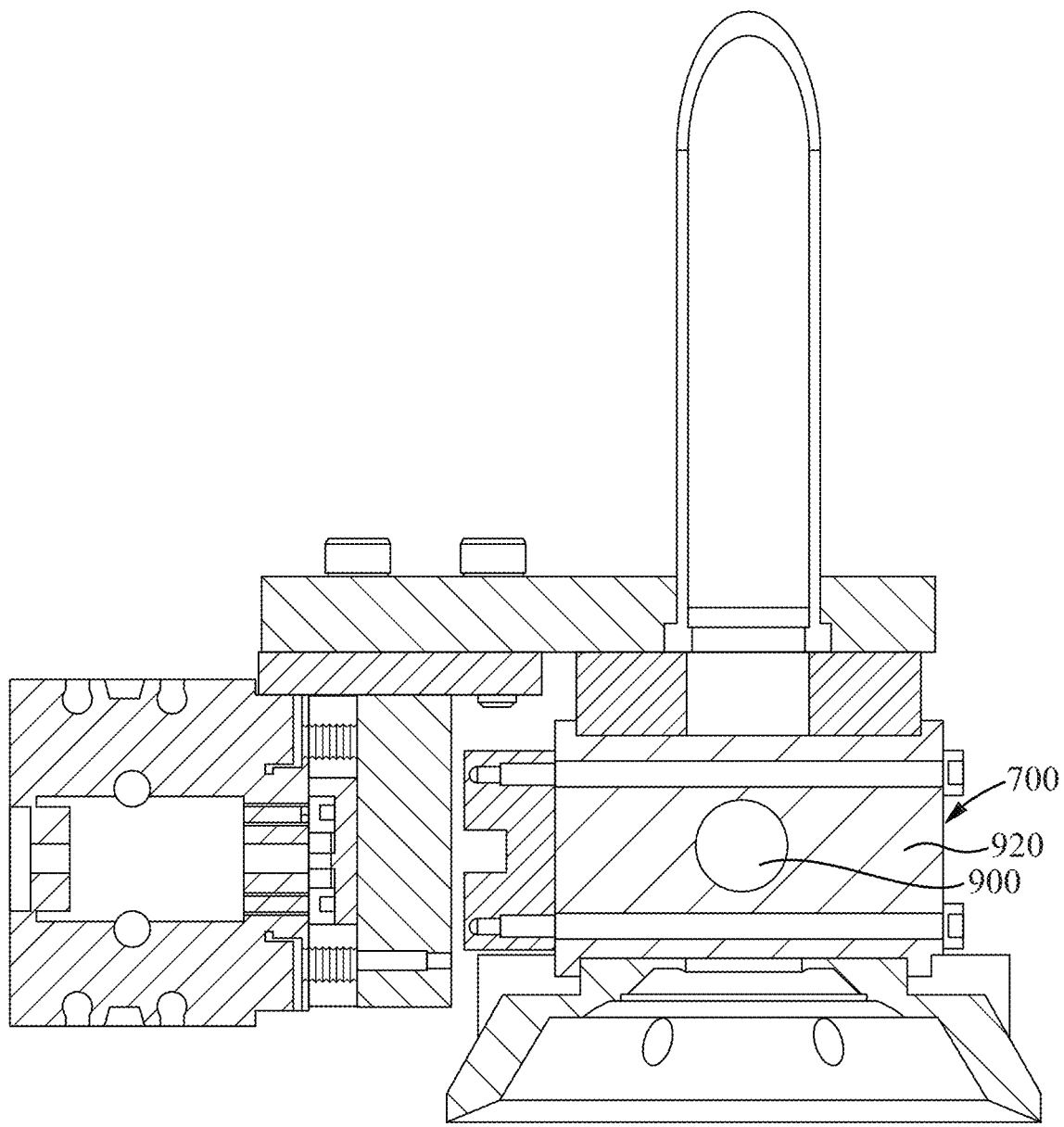
Figs. 8A, 8B, and 8C are cross-sectional views of the shutoff valve assembly along line 8A 8B 8C-8A 8B 8C.
Figure 8B:
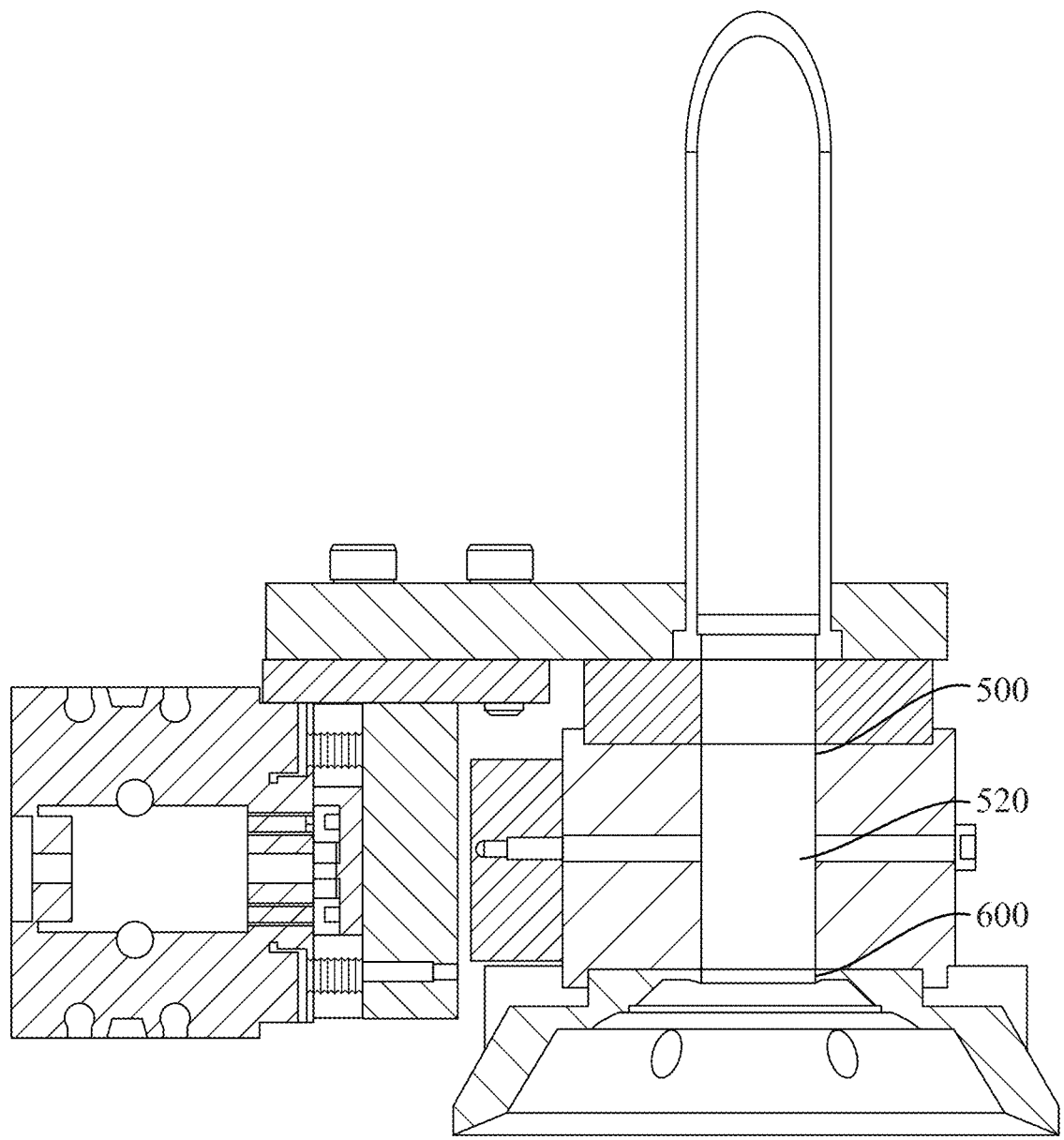
Figure 8C:
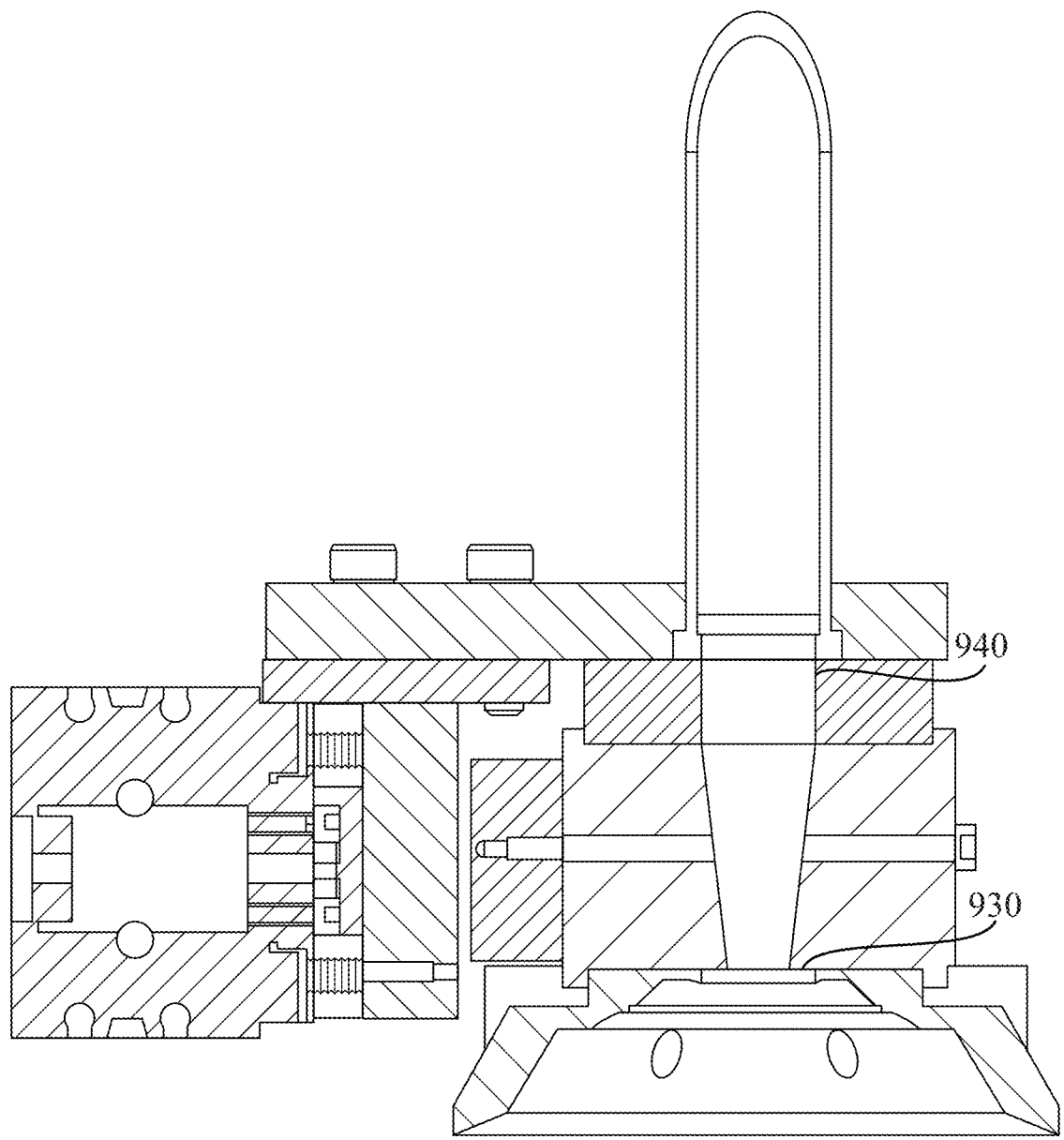
Figure 9A:
FIG. 9A demonstrates the Visual Opaque Evaluation test and shows the 2 samples side by side.
Figure 9B:
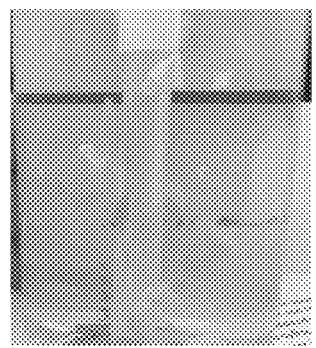
FIG. 9B demonstrates the Visual Opaque Evaluation test and shows the non-aerated product with the "3"s printed behind.
Figure 9C:
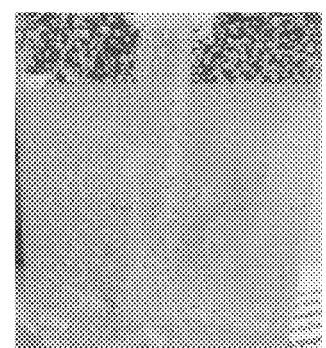
FIG. 9C demonstrates the Visual Opaque Evaluation test and shows the aerated product with the "3"s printed behind.
Figure 10A:
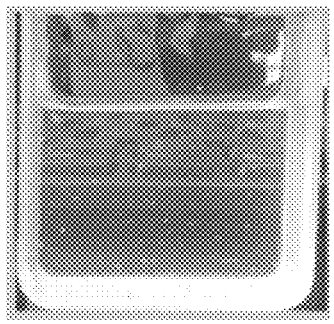
FIG. 10A demonstrates an image of shampoos without bubbles.
Figure 10B:
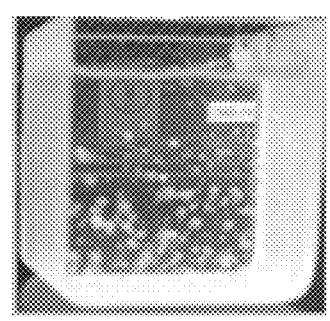
FIG. 10B demonstrates an image of shampoos with some bubbles.
Figure 10C:
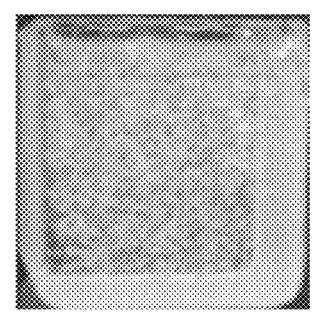
FIG. 10C demonstrates an image of shampoos with many bubbles.

Product 300 is filled into bottles 310 (FIG. 7 through a filling nozzle 320). Filling nozzles typically include a positive method of shutting off the flow between filling cycles. This is done to prevent or minimize the amount of dripping or stringing of product out of the nozzle in between filling cycles. Without this strategy it is common to have product filling on the outside of the bottle which is undesirable for consumer aesthetics, cleanliness, and product waste reasons. The method of shutting off the flow between filling cycles is typically a piston device that is positioned inside of the filling nozzle. The piston raises and lowers between filling cycles. It is found that microcapsules can become blocked from flowing around this piston resulting in microcapsules flowing predominately down on side of the filler nozzle. This is found to result in microcapsules tending to align on one side of the bottle more than the other side giving a non-uniform microcapsule appearance that is not desired. Therefore, a filling nozzle may be used to minimize damage and to assist with distributing microcapsules throughout the filled bottle. Figs. 8A 8B and 8C each show a cross-section view of the filling nozzle along line 8A 8B 8C-8A 8B 8C. The filling nozzle can comprise a fluid shutoff valve assembly 400, the valve assembly having a fluid flow path defining a direction of fluid flow, the assembly comprising: a fluid inlet orifice 500 in fluid communication with a source of a fluid, the fluid inlet orifice allowing the fluid to flow in the direction of fluid flow from the source of the fluid into the fluid flow path of the valve assembly; a fluid outlet orifice 600 in fluid communication with the fluid flow path of the valve assembly and through which the fluid may flow out of the valve assembly; and a fluid shutoff valve 700 in fluid communication with the fluid inlet and the fluid outlet, the fluid shutoff valve having a fluid blocking portion 920 and a fluid flow-through portion 900, the fluid shutoff valve being moveable from a filling position (as shown in FIGS. 8B and 8C) wherein the fluid flowthrough portion is aligned with the fluid flow path to a closed position wherein the fluid blocking portion is aligned with the fluid flow path, wherein the fluid shutoff valve is oriented such that it moves in a direction that is generally perpendicular to the direction of fluid flow at a location where the fluid shutoff valve intercepts the fluid flow path. Suitable filling nozzles are disclosed in U.S. Pat. No. 9,720,425. Additionally, the fluid shutoff valve can be moveable to a closed position, wherein the fluid is blocked from flowing through the fluid flow path (as shown in FIG. 8A). The fluid shutoff valve 400 rotates along access 420, to the open position (shown in FIGS. 8B and 8C) to the closed position (as shown in FIG. 8A).

The fluid flow-through portion has an upper portion in contact with the fluid inlet 500, a middle portion 520, and a lower portion 600 in contact with the fluid outlet. All three portions of the fluid flow-through can have the same diameter (as shown in FIG. 8B), alternatively the lower portion 930 of the fluid flow-through can have a smaller diameter than the upper portion 940 of the fluid flow-through (as shown in FIG. 8C). The upper portion of the fluid flow-through can have the same diameter as the fluid inlet, and the lower portion of the fluid flow-through can have the same diameter as the fluid outlet (as shown in FIG. 8B).

Additionally, the fluid nozzles can be modified or changed out between production runs to set a fluid velocity leaving the nozzle. The fluid velocity can provide optimal flow conditions in the bottle. Too slow of a fluid velocity leaving the nozzle can result in microcapsules that are not uniformly distributed in the bottle. Too fast of a fluid velocity can result in too much air incorporation or splashing.

B. Microcapsules

The shampoo product contains microcapsules. The microcapsules can have a round, bead like, lamellar or strip-like, sheet, spherical, semi-spherical, hemi-spherical, flat bottomed tear drop, ellipsoidal or ribbon like form. The shampoo product comprises from about 0.05 wt % to about 10 wt %, alternatively from about 0.1 wt % to about 5 wt % of microcapsules. They can have a thickness less than the width, with a thickness of from about 0.01 to about 1 mm, alternatively from about 0.4 to about 0.8 mm (measurement at the middle of the sheet). The microcapsules can be about 0.5 mm to about 20 mm in width and/or length, alternatively from about 1 mm to about 5 mm, alternatively from about 5 mm to about 20 mm in width and/or length, alternatively from about 8 mm to about 15 mm in width and/or length. The shape can be any geometric shape, including but not limited to circular (FIG. 5A), petal (FIG. 5B) triangular (FIG. 5C), rectangular (FIG. 5D), oblong (FIG. 5E), and/or square (FIG. 5F).

The microcapsules can be a gellan film and comprise from about 30 to about 40 parts of sodium alginate, from about 40 to about 50 parts gellan gum, from about 5 to about 10 parts polyvinyl alcohol, from about 5 to about 10 parts hydroxyl methyl cellulose sodium. The microcapsules may also comprise menthol, peppermint oil, menthyl lactate, jojoba oil, Vitamin E as well as dyes, other extracts and/or perfumes. Suitable microcapsules, Dream Petals, are available from Sandream Impact LLC, Fairfield New Jersey. Suitable microcapsules in bead form include, but are not limited to, Koko Products Incorporated of South Plainfield NJ, Scrubbing Beads, Floratech Cosmetics of Chandler, AZ Ecobeads, Florabeads, and Florasomes.

Alternatively, the microcapsules in the personal care composition can be discrete particles that comprise anhydrous particles and an aqueous phase, such as those disclosed in US Patent Application 2019/035485. The anhydrous particles are prepared by co-melting one or more fatty amphiphile and one or more secondary surfactants and then cooled to solidify. Various methodologies can be used to control the particle size of such anhydrous particles. The anhydrous particles are then added into an aqueous phase that contains detersive surfactant. This results in the swelling of such particles transforming them into discrete particles. The discrete particle can be a gel network.

The size of the discrete particles in the cleansing composition ranges from about 200 µm to about 15,000 µm. Alternatively, the scale size of the discrete particles in the cleansing composition ranges from about 500 µm to about 7000 µm. Alternatively, the scale size of the discrete particles in the cleansing composition ranges from about 1000 µm to about 5000 µm. As measured by conventional techniques, visually via ruler, light microscopy etc.

C. Incorporation of Microcapsules into a Personal Care Product

1. Personal Care Chassis

The personal care compositions can be made by forming a personal care chassis comprising water, surfactants and optionally thickeners, stabilizing agents, thickening agents, polymers, conditioning agents, perfumes and preservative agents. The microcapsules can then be added via the method previously described.

a. Surfactant

The personal care compositions described herein can include one or more surfactants in the surfactant system. The one or more surfactants can be selected from the group consisting of anionic surfactants, amphoteric surfactants, nonionic surfactants and mixtures thereof. The one or more surfactants can be substantially free of sulfate-based surfactants. As can be appreciated, surfactants provide a cleaning benefit to soiled articles such as hair, skin, and hair follicles by facilitating the removal of oil and other soils. Surfactants generally facilitate such cleaning due to their amphiphilic nature which allows for the surfactants to break up, and form micelles around, oil and other soils which can then be rinsed out, thereby removing them from the soiled article. Suitable surfactants for a personal care composition can include anionic moieties to allow for the formation of a coacervate with a cationic polymer. The surfactant can be selected from anionic surfactants, amphoteric surfactants, zwitterionic surfactants, non-ionic surfactants, and combinations thereof.

The personal care composition comprises one or more detersive surfactants in the personal care base. The detersive surfactant component is included in personal care compositions to provide cleansing performance. The detersive surfactant may be selected from anionic detersive surfactant, zwitterionic, or amphoteric detersive surfactant, or a combination thereof. Such surfactants should be physically and chemically compatible with the components described herein, or should not otherwise unduly impair product stability, aesthetics or performance. Particularly suitable herein is sodium laureth-n-sulfate, wherein n=1 ("SLE1S"). SLE1S enables more efficient lathering and cleaning when compared to higher mole ethoxylate equivalents, especially in a personal care composition that contains high levels of conditioning actives.

Suitable anionic detersive surfactants include those which are known for use in hair care or other personal care personal care compositions. The anionic detersive surfactant may be a combination of sodium lauryl sulfate and sodium laureth-n sulfate. The concentration of the anionic surfactant in the composition should be sufficient to provide the desired cleaning and lather performance, and generally range from about 5% to about 50%, alternatively from about 8% to about 30%, alternatively from about 9% to about 25%, and alternatively from about 10% to about 17%, by weight of the composition.

Suitable zwitterionic or amphoteric detersive surfactants include those which are known for use in hair care or other personal care compositions. Concentration of such amphoteric detersive surfactants range from about 0.5% to about 20%, alternatively from about 1% to about 10%. Non-limiting examples of suitable zwitterionic or amphoteric surfactants are described in U.S. Pat. Nos. 5,104,646 and 5,106,609.

Additional anionic surfactants suitable for use herein include alkyl and alkyl ether sulfates of the formula $ROSO_3M$ and $RO(C_2H_4O)_xSO_3M$, wherein R is alkyl or alkenyl of from about 8 to about 18 carbon atoms, x is 1 to 10, and M is a water-soluble cation such as ammonium, sodium, potassium, and triethanolamine cation or salts of the divalent magnesium ion with two anionic surfactant anions. The alkyl ether sulfates may be made as condensation products of ethylene oxide and monohydric alcohols having from about 8 to about 24 carbon atoms. The alcohols can be derived from fats such as coconut oil, palm oil, palm kernel oil, or tallow, or can be synthetic.

Examples of additional anionic surfactants suitable for use include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium trideceth sulfate, sodium tridecyl sulfate, sodium methyl lauroyl taurate, sodium methyl cocoyl taurate, sodium lauroyl isethionate, sodium cocoyl isethionate, sodium laurethsulfosuccinate, sodium laurylsulfosuccinate, sodium tridecyl benzene sulfonate, sodium dodecyl benzene sulfonate, and mixtures thereof.

The personal care composition may further comprise additional surfactants for use in combination with the anionic detersive surfactant component described herein. Suitable additional surfactants include cationic and nonionic surfactants.

Non-limiting examples of other anionic, zwitterionic, amphoteric, cationic, nonionic, or optional additional surfactants suitable for use in the compositions are described in McCutcheon's, Emulsifiers and Detergents, 1989 Annual, published by M. C. Publishing Co., and U.S. Pat. Nos. 3,929,678; 2,658,072; 2,438,091; and 2,528,378.

The personal care compositions described herein can be substantially free of sulfate-based surfactants. "Substantially free" of sulfate based surfactants as used herein means from about 0 wt % to about 3 wt %, alternatively from about 0 wt % to about 2 wt %, alternatively from about 0 wt % to about 1 wt %, alternatively from about 0 wt % to about 0.5 wt %, alternatively from about 0 wt % to about 0.25 wt %, alternatively from about 0 wt % to about 0.1 wt %, alternatively from about 0 wt % to about 0.05 wt %, alternatively from about 0 wt % to about 0.01 wt %, alternatively from about 0 wt % to about 0.001 wt %, and/or alternatively free of sulfates. As used herein, "free of" means 0 wt %.

The one or more additional anionic surfactants may be selected from the group consisting of isethionates, sarcosinates, sulfonates, sulfosuccinates, sulfoacetates, acyl glycinates, acyl alaninates, acyl glutamates, lactates, lactylates, glucose carboxylates, amphoacetates, taurates, phosphate esters, and mixtures thereof. In that case, alkyl is defined as a saturated or unsaturated, straight or branched alkyl chain with 7 to 17 carbon atoms, alternatively with 9 to 13 carbon atoms. In that case, acyl is defined as of formula R—C(O)—, wherein R is a saturated or unsaturated, straight or branched alkyl chain with 7 to 17 carbon atoms, alternatively with 9 to 13 carbon atoms.

Suitable isethionate surfactants can include the reaction product of fatty acids esterified with isethionic acid and neutralized with sodium hydroxide. Suitable fatty acids for isethionate surfactants can be derived from coconut oil or palm kernel oil including amides of methyl tauride.

Non-limiting examples of isethionates can be selected from the group consisting of sodium lauroyl methyl isethionate, sodium cocoyl isethionate, ammonium cocoyl isethionate, sodium hydrogenated cocoyl methyl isethionate, sodium lauroyl isethionate, sodium cocoyl methyl isethionate, sodium myristoyl isethionate, sodium oleoyl isethionate, sodium oleyl methyl isethionate, sodium palm kerneloyl isethionate, sodium stearoyl methyl isethionate, and mixtures thereof.

Non-limiting examples of sarcosinates can be selected from the group consisting of sodium lauroyl sarcosinate, sodium cocoyl sarcosinate, sodium myristoyl sarcosinate, TEA-cocoyl sarcosinate, ammonium cocoyl sarcosinate, ammonium lauroyl sarcosinate, dimer dilinoleyl bis-lauroyl-glutamate/lauroylsarcosinate, disodium lauroamphodiacetate, lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and combinations thereof.

Non-limiting examples of sulfosuccinate surfactants can include disodium N-octadecyl sulfosuccinate, disodium lauryl sulfosuccinate, diammonium lauryl sulfosuccinate, sodium lauryl sulfosuccinate, disodium laureth sulfosuccinate, tetrasodium N-(1,2-dicarboxyethyl)-N-octadecyl sulfosuccinnate, diamyl ester of sodium sulfosuccinic acid, dihexyl ester of sodium sulfosuccinic acid, dioctyl esters of sodium sulfosuccinic acid, and combinations thereof.

Non-limiting examples of sulfoacetates can include sodium lauryl sulfoacetate, ammonium lauryl sulfoacetate and combination thereof.

Non-limiting examples of acyl glycinates can include sodium cocoyl glycinate, sodium lauroyl glycinate and combination thereof.

Non-limiting example of acyl alaninates can include sodium cocoyl alaninate, sodium lauroyl alaninate, sodium N-dodecanoyl-l-alaninate and combinations thereof.

Non-limiting examples of acyl glutamates can be selected from the group consisting of sodium cocoyl glutamate, disodium cocoyl glutamate, ammonium cocoyl glutamate, diammonium cocoyl glutamate, sodium lauroyl glutamate, disodium lauroyl glutamate, sodium cocoyl hydrolyzed wheat protein glutamate, disodium cocoyl hydrolyzed wheat protein glutamate, potassium cocoyl glutamate, dipotassium cocoyl glutamate, potassium lauroyl glutamate, dipotassium lauroyl glutamate, potassium cocoyl hydrolyzed wheat protein glutamate, dipotassium cocoyl hydrolyzed wheat protein glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallow glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallow glutamate, sodium cocoyl/palmoyl/sunfloweroyl glutamate, sodium hydrogenated tallowoyl glutamate, sodium olivoyl glutamate, disodium olivoyl glutamate, sodium palmoyl glutamate, disodium palmoyl glutamate, TEA-cocoyl glutamate, TEA-hydrogenated tallowoyl glutamate, TEA-lauroyl glutamate, and mixtures thereof.

Non-limiting examples of acyl glycinates can include sodium cocoyl glycinate, sodium lauroyl glycinate and combination thereof.

Non-limiting example of lactates can include sodium lactate.

Non-limiting examples of lactylates can include sodium lauroyl lactylate, sodium cocoyl lactylate and combination thereof.

Non-limiting examples of glucose carboxylates can include sodium lauryl glucoside carboxylate, sodium cocoyl glucoside carboxylate and combinations thereof.

Non-limiting examples of alkylamphoacetates can include sodium cocoyl amphoacetate, sodium lauroyl amphoacetate and combination thereof.

Non-limiting examples of acyl taurates can include sodium methyl cocoyl taurate, sodium methyl lauroyl taurate, sodium methyl oleoyl taurate and combination thereof.

Co-surfactants are materials which are combined with the undecyl sulfate surfactant and optionally anionic surfactants to enhance lather volume and/or to modify lather texture. Typically these materials can be selected from a variety of families of structures including, but not limited to, amphoteric, zwitterionic, cationic, and nonionic. They are typically used with anionic surfactants in a weight ratio of 1:20 to 1:4, and alternatively in the 1:12 to 1:7 weight ratio.

The personal care composition may comprise from about 0.5 wt % to about 10 wt %, alternatively from about 0.5 wt % to about 5 wt %, alternatively from about 0.5 wt % to about 3 wt %, alternatively from about 0.5 wt % to about 2 wt %, and alternatively from about 0.5 wt % to about 1.75 wt % by weight of the composition of at least one suitable co-surfactant. The co-surfactant may serve to produce faster lather, facilitate easier rinsing, and/or mitigate harshness on the keratinous tissue. The co-surfactant further may aid in producing lather having more desirable texture, volume and/or other properties.

Amphoteric surfactants suitable for use herein include, but are not limited, to derivatives of aliphatic secondary and tertiary amines in which the aliphatic radical can be straight or branched chain and wherein one substituent of the aliphatic substituents contains from about 8 to about 18 carbon atoms and one contains an anionic water solubilizing group, e.g., carboxy, sulfonate, sulfate, phosphate, or phosphonate. Examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No.2,528,378, and mixtures thereof. The amphoteric surfactants may selected from the family of betaines such as lauryolamphoacetate.

Zwitterionic surfactants suitable for use herein include, but are not limited, to derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Other zwitterionic surfactants suitable for use herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. The sulfobetaines may include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof. Other suitable amphoteric surfactants include amidobetaines and amidosulfobetaines, wherein the RCONH $(CH_2)_3$ radical, wherein R is a $C_{11}$-$C_{17}$ alkyl, is attached to the nitrogen atom of the betaine.

Nonionic co-surfactants suitable for use in the composition for enhancing lather volume or texture include water soluble materials like lauryl dimethylamine oxide, cocodimethylamine oxide, cocoamidopropylamine oxide, laurylamidopropyl amine oxide, etc. or alkylpolyethoxylates like laureth-4 to laureth-7 and water insoluble components such as cocomonoethanol amide, cocodiethanol amide, lauroylmonoethanol amide, alkanoyl isopropanol amides, and fatty alcohols like cetyl alcohol and oleyl alcohol, and 2-hydroxyalkyl methyl ethers, etc.

Further suitable materials as co-surfactants herein include 1,2-alkylepoxides, 1,2-alkanediols, branched or straight chain alkyl glyceryl ethers (e.g., as disclosed in EP 1696023A1), 1,2-alkylcyclic carbonates, and 1,2-alkyl cyclicsulfites, particularly those wherein the alkyl group contains 6 to 14 carbon atoms in linear or branched configuration. Other examples include the alkyl ether alcohols derived from reacting $C_{10}$ or $C_{12}$ alpha olefins with ethylene glycol (e.g., hydroxyethyl-2-decyl ether, hydroxyethyl-2-dodecyl ether), as can be made according to U.S. Pat. Nos. 5,741,948; 5,994,595; 6,346,509; and 6,417,408.

Other nonionic surfactants may be selected from the group consisting of glucose amides, alkyl polyglucosides, sucrose cocoate, sucrose laurate, alkanolamides, ethoxylated alcohols and mixtures thereof. The nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

The co-surfactant can be selected from the group consisting of Cocomonoethanol Amide, Cocoamidopropyl Betaine, Laurylamidopropyl Betaine, Cocobetaine, lauryl betaine, lauryl amine oxide, sodium lauryl amphoacetate; alkyl glyceryl ethers, alkyl-di-glyceryl ethers, 1,2-alkyl cyclic sulfites, 1,2-alkyl cyclic carbonates, 1,2-alkyl-epoxides, alkyl glycidylethers, and alkyl-1,3-dioxalanes, wherein the alkyl group contains 6 to 14 carbon atoms in linear or branched configuration; 1,2-alkane diols where the total carbon content is from 6 to 14 carbon atoms linear or branched, methyl-2-hydroxy-decyl ethers, hydroxyethyl-2-dodecyl ether, hydroxyethyl-2-decyl ether, and mixtures thereof.

Cationic surfactants may be derived from amines that are protonated at the pH of the formulation, e.g. bis-hydroxyethyl lauryl amine, lauryl dimethylamine, lauroyl dimethyl amidopropyl amine, cocoylamidopropyl amine, and the like. The cationic surfactants may also be derived from fatty quaternary ammonium salts such as lauryl trimethylammonium chloride and lauroylamidopropyl trimethyl ammonium chloride.

Alkylamphoacetates are suitable surfactants used in the compositions herein for improved product mildness and lather. The most commonly used alkylamphoacetates are lauroamphoacetate and cocoamphoacetate. Alkylamphoacetates can be comprised of monoacetates and diacetates. In some types of alkylamphoacetates, diacetates are impurities or unintended reaction products. However, the presence of diacetate can cause a variety of unfavorable composition characteristics when present in amounts over 15% of the alkylamphoacetates.

Suitable nonionic surfactants for use herein are those selected from the group consisting of glucose amides, alkyl polyglucosides, sucrose cocoate, sucrose laurate, alkanolamides, ethoxylated alcohols and mixtures thereof. In one embodiment the nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

Non-limiting examples of suitable structurants are described in U.S. Pat. No. 5,952,286, and include unsaturated and/or branched long chain ($C_8$-$C_{24}$) liquid fatty acids or ester derivative thereof; unsaturated and/or branched long chain liquid alcohol or ether derivatives thereof, and mixtures thereof. The surfactant also may comprise short chain saturated fatty acids such as capric acid and caprylic acid. Without being limited by theory, it is believed that the unsaturated part of the fatty acid of alcohol or the branched part of the fatty acid or alcohol acts to "disorder" the surfactant hydrophobic chains and induce formation of lamellar phase. Examples of suitable liquid fatty acids include oleic acid, isostearic acid, linoleic acid, linolenic acid, ricinoleic acid, elaidic acid, arichidonic acid, myristoleic acid, palmitoleic acid, and mixtures thereof. Examples of suitable ester derivatives include propylene glycol isostearate, propylene glycol oleate, glyceryl isostearate, glyceryl oleate, polyglyceryl diisostearate and mixtures thereof. Examples of alcohols include oleyl alcohol and isostearyl alcohol. Examples of ether derivatives include isosteareth or oleth carboxylic acid; or isosteareth or oleth alcohol. The structuring agent may be defined as having melting point below about 25° C.

If present, the composition may comprise a rheology modifier, wherein said rheology modifier comprises cellulosic rheology modifiers, cross-linked acrylates, cross-linked maleic anhydride co-methylvinylethers, hydrophobically modified associative polymers, or a mixture thereof.

An electrolyte, if used, can be added per se to the composition or it can be formed in situ via the counterions included in one of the raw materials. The electrolyte may include an anion comprising phosphate, chloride, sulfate or citrate and a cation comprising sodium, ammonium, potassium, magnesium or mixtures thereof. The electrolyte may be sodium chloride, ammonium chloride, sodium or ammonium sulfate. The electrolyte may be added to the composition in the amount of from about 0.1 wt % to about 15 wt % by weight, alternatively from about 1 wt % to about 6 wt % by weight, and alternatively from about 3 wt % to about 6 wt %, by weight of the composition.

b. Cationic Polymer

A personal care composition can include a cationic polymer to allow formation of a coacervate. As can be appreciated, the cationic charge of a cationic polymer can interact with an anionic charge of a surfactant to form the coacervate. Suitable cationic polymers can include: (a) a cationic guar polymer, (b) a cationic non-guar galactomannan polymer, (c) a cationic starch polymer, (d) a cationic copolymer of acrylamide monomers and cationic monomers, (e) a synthetic, non-crosslinked, cationic polymer, which may or may not form lyotropic liquid crystals upon combination with the detersive surfactant, (f) cationic synthetic homopolymers, (g) a cationic cellulose polymer, and (h) combinations thereof. In certain examples, more than one cationic polymer can be included. The cationic polymer can be selected from guar hydroxypropyltrimonium chloride, Polyquaterium 10, Polyquaternium 6, and combinations thereof.

A cationic polymer can be included by weight of the personal care composition at about 0.05% to about 3%, about 0.075% to about 2.0%, or at about 0.1% to about 1.0%. Cationic polymers can have cationic charge densities of about 0.9 meq/g or more, about 1.2 meq/g or more, and about 1.5 meq/g or more. However, cationic charge density can also be about 7 meq/g or less and alternatively about 5 meq/g or less. The charge densities can be measured at the pH of intended use of the personal care composition. (e.g., at about pH 3 to about pH 9; or about pH 4 to about pH 8). The average molecular weight of cationic polymers can generally be between about 10,000 and 10 million, between about 50,000 and about 5 million, and between about 100,000 and about 3 million, and between about 300,000 and about 3 million and between about 100,000 and about 2.5 million. Low molecular weight cationic polymers can be used. Low molecular weight cationic polymers can have greater translucency in the liquid carrier of a personal care composition. The cationic polymer can be a single type, such as the cationic guar polymer guar hydroxypropyltrimonium chloride having a weight average molecular weight of about 2.5 million g/mol or less, and the personal care composition can have an additional cationic polymer of the same or different types.

Cationic Guar Polymer

The cationic polymer can be a cationic guar polymer, which is a cationically substituted galactomannan (guar) gum derivative. Suitable guar gums for guar gum derivatives can be obtained as a naturally occurring material from the seeds of the guar plant. As can be appreciated, the guar molecule is a straight chain mannan which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums can be obtained through reactions between the hydroxyl groups of the polygalactomannan and reactive quaternary ammonium compounds. The degree of substitution of the cationic groups onto the guar structure can be sufficient to provide the requisite cationic charge density described above.

A cationic guar polymer can have a weight average molecular weight ("M.Wt.") of less than about 3 million g/mol, and can have a charge density from about 0.05 meq/g to about 2.5 meq/g. Alternatively, the cationic guar polymer can have a weight average M.Wt. of less than 1.5 million g/mol, from about 150 thousand g/mol to about 1.5 million g/mol, from about 200 thousand g/mol to about 1.5 million g/mol, from about 300 thousand g/mol to about 1.5 million g/mol, and from about 700,000 thousand g/mol to about 1.5 million g/mol. The cationic guar polymer can have a charge density from about 0.2 meq/g to about 2.2 meq/g, from about 0.3 meq/g to about 2.0 meq/g, from about 0.4 meq/g to about 1.8 meq/g; and from about 0.5 meq/g to about 1.7 meq/g.

A cationic guar polymer can have a weight average M.Wt. of less than about 1 million g/mol, and can have a charge density from about 0.1 meq/g to about 2.5 meq/g. A cationic guar polymer can have a weight average M.Wt. of less than 900 thousand g/mol, from about 150 thousand to about 800 thousand g/mol, from about 200 thousand g/mol to about 700 thousand g/mol, from about 300 thousand to about 700 thousand g/mol, from about 400 thousand to about 600 thousand g/mol, from about 150 thousand g/mol to about 800 thousand g/mol, from about 200 thousand g/mol to about 700 thousand g/mol, from about 300 thousand g/mol to about 700 thousand g/mol, and from about 400 thousand g/mol to about 600 thousand g/mol. A cationic guar polymer has a charge density from about 0.2 meq/g to about 2.2 meq/g, from about 0.3 meq/g to about 2.0 meq/g, from about 0.4 meq/g to about 1.8 meq/g; and from about 0.5 meq/g to about 1.5 meq/g.

A personal care composition can include from about 0.01% to less than about 0.7%, by weight of the personal care composition of a cationic guar polymer, from about 0.04% to about 0.55%, by weight, from about 0.08% to about 0.5%, by weight, from about 0.16% to about 0.5%, by weight, from about 0.2% to about 0.5%, by weight, from about 0.3% to about 0.5%, by weight, and from about 0.4% to about 0.5%, by weight.

The cationic guar polymer can be formed from quaternary ammonium compounds which conform to general Formula II:

Formula II wherein where $R^3$, $R^4$ and $R^5$ are methyl or ethyl groups; and $R^6$ is either an epoxyalkyl group of the general Formula III:

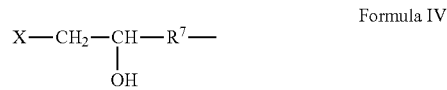

Formula III or $R^6$ is a halohydrin group of the general Formula IV: wherein $R^7$ is a $C_1$ to $C_3$ alkylene;

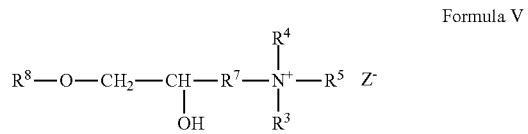

Formula IV

X is chlorine or bromine, and Z is an anion such as Cl—, Br—, I— or $HSO_4$—.

Suitable cationic guar polymers can conform to the general formula V:

Formula V wherein $R^8$ is guar gum; and wherein $R^4$, $R^5$, $R^6$ and $R^7$ are as defined above; and wherein Z is a halogen. Suitable cationic guar polymers can conform to Formula VI:

$$R^8\text{—O—CH}_2\text{—CH—CH}_2N^+(CH_3)_3Cl^-$$
$$|$$
$$OH$$

Formula VI wherein $R^8$ is guar gum.

Suitable cationic guar polymers can also include cationic guar gum derivatives, such as guar hydroxypropyltrimonium chloride. Suitable examples of guar hydroxypropyltrimonium chlorides can include the Jaguar® series commercially available from Solvay S.A., Hi-Care Series from Rhodia, and N-Hance and AquaCat from Ashland Inc. Jaguar® C-500 has a charge density of 0.8 meq/g and a M.Wt. of 500,000 g/mole; Jaguar Optima has a cationic charge density of about 1.25 meg/g and a M.Wt. of about 500,000 g/moles; Jaguar® C-17 has a cationic charge density of about 0.6 meq/g and a M.Wt. of about 2.2 million g/mol; Jaguar® and a cationic charge density of about 0.8 meq/g; Hi-Care 1000 has a charge density of about 0.7 meq/g and a M.Wt. of about 600,000 g/mole; N-Hance 3269 and N-Hance 3270, have a charge density of about 0.7 meq/g and a M.Wt. of about 425,000 g/mole; N-Hance 3196 has a charge density of about 0.8 meq/g and a M.Wt. of about 1,100,000 g/mole; and AquaCat CG518 has a charge density of about 0.9 meq/g and a M.Wt. of about 50,000 g/mole. N-Hance BF-13 and N-Hance BF-17 are borate (boron) free guar polymers. N-Hance BF-13 has a charge density of about 1.1 meq/g and M.W.t of about 800,000 and N-Hance BF-17 has a charge density of about 1.7 meq/g and M.W.t of about 800,000. BF-17 has a charge density of about 1.7 meq/g and M.W.t of about 800,000. BF-17 has a charge density of about 1.7 meq/g and M.W.t of about 800,000. BF-17 has a charge density of about 1.7 meq/g and M.W.t of about 800,000. BF-17 has a charge density of about 1.7 meq/g and M.W.t of about 800,000.

Cationic Non-Guar Galactomannan Polymer

The cationic polymer can be a galactomannan polymer derivative. Suitable galactomannan polymer can have a mannose to galactose ratio of greater than 2:1 on a monomer to monomer basis and can be a cationic galactomannan polymer derivative or an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers can be present in the endosperm of seeds of the Leguminosae family Galactomannan polymers are made up of a combination of mannose monomers and galactose monomers. The galactomannan molecule is a straight chain mannan branched at regular intervals with single membered galactose units on specific mannose units. The mannose units are linked to each other by means of β(1-4) glycosidic linkages. The galactose branching arises by way of an α(1-6) linkage. The ratio of mannose monomers to galactose monomers varies according to the species of the plant and can be affected by climate. Non Guar Galactomannan polymer derivatives can have a ratio of mannose to galactose of greater than 2:1 on a monomer to monomer basis. Suitable ratios of mannose to galactose can also be greater than 3:1 or greater than 4:1. Analysis of mannose to galactose ratios is well known in the art and is typically based on the measurement of the galactose content.

The gum for use in preparing the non-guar galactomannan polymer derivatives can be obtained from naturally occurring materials such as seeds or beans from plants. Examples of various non-guar galactomannan polymers include Tara gum (3 parts mannose/1 part galactose), Locust bean or Carob (4 parts mannose/1 part galactose), and Cassia gum (5 parts mannose/1 part galactose).

A non-guar galactomannan polymer derivative can have a M. Wt. from about 1,000 g/mol to about 10,000,000 g/mol, and a M.Wt. from about 5,000 g/mol to about 3,000,000 g/mol.

The personal care compositions described herein can include galactomannan polymer derivatives which have a cationic charge density from about 0.5 meq/g to about 7 meq/g. The galactomannan polymer derivatives can have a cationic charge density from about 1 meq/g to about 5 meq/g. The degree of substitution of the cationic groups onto the galactomannan structure can be sufficient to provide the requisite cationic charge density.

A galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general Formulas II to VI, as defined above.

Cationic non-guar galactomannan polymer derivatives formed from the reagents described above can be represented by the general Formula VII:

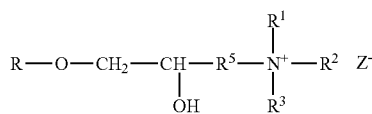

Formula VII wherein R is the gum. The cationic galactomannan derivative can be a gum hydroxypropyltrimethylammonium chloride, which can be more specifically represented by the general Formula VIII:

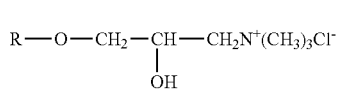

Formula VIII

The galactomannan polymer derivative can be an amphoteric galactomannan polymer derivative having a net positive charge, obtained when the cationic galactomannan polymer derivative further comprises an anionic group.

A cationic non-guar galactomannan can have a ratio of mannose to galactose which is greater than about 4:1, a M.Wt. of about 100,000 g/mol to about 500,000 g/mol, a M.Wt. of about 50,000 g/mol to about 400,000 g/mol, and a cationic charge density from about 1 meq/g to about 5 meq/g, and from about 2 meq/g to about 4 meq/g.

Personal care compositions can include at least about 0.05% of a galactomannan polymer derivative by weight of the composition. The personal care compositions can include from about 0.05% to about 2%, by weight of the composition, of a galactomannan polymer derivative.

Cationic Starch Polymers

Suitable cationic polymers can also be water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The personal care compositions described herein can include cationically modified starch polymers at a range of about 0.01% to about 10%, and/or from about 0.05% to about 5%, by weight of the composition.

The cationically modified starch polymers disclosed herein have a percent of bound nitrogen of from about 0.5% to about 4%.

The cationically modified starch polymers can have a molecular weight from about 850,000 g/mol to about 15,000,000 g/mol and from about 900,000 g/mol to about 5,000,000 g/mol.

Cationically modified starch polymers can have a charge density of from about 0.2 meq/g to about 5 meq/g, and from about 0.2 meq/g to about 2 meq/g. The chemical modification to obtain such a charge density can include the addition of amino and/or ammonium groups into the starch molecules. Non-limiting examples of such ammonium groups can include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. Further details are described in Solarek, D. B., Cationic Starches in Modified Starches: Properties and Uses, Wurzburg, O. B., Ed., CRC Press, Inc., Boca Raton, Fla. 1986, pp 113-125 which is hereby incorporated by reference. The cationic groups can be added to the starch prior to degradation to a smaller molecular weight or the cationic groups may be added after such modification.

A cationically modified starch polymer can have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution can be determined using proton nuclear magnetic resonance spectroscopy ("$^1$H NMR") methods well known in the art. Suitable $^1$H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be selected from a variety of sources such as tubers, legumes, cereal, and grains. For example, starch sources can include corn starch, wheat starch, rice starch, waxy corn starch, oat starch, cassaya starch, waxy barley, waxy rice starch, glutenous rice starch, sweet rice starch, amioca, potato starch, tapioca starch, oat starch, sago starch, sweet rice, or mixtures thereof. Suitable cationically modified starch polymers can be selected from degraded cationic maize starch, cationic tapioca, cationic potato starch, and mixtures thereof. Cationically modified starch polymers are cationic corn starch and cationic tapioca.

The starch, prior to degradation or after modification to a smaller molecular weight, can include one or more additional modifications. For example, these modifications may include cross-linking, stabilization reactions, phosphorylations, and hydrolyzations. Stabilization reactions can include alkylation and esterification.

Cationically modified starch polymers can be included in a personal care composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

The starch can be readily soluble in water and can form a substantially translucent solution in water. The transparency of the composition is measured by Ultra-Violet/Visible ("UV/VIS") spectrophotometry, which determines the absorption or transmission of UV/VIS light by a sample, using a Gretag Macbeth Colorimeter Color. A light wavelength of 600 nm has been shown to be adequate for characterizing the degree of clarity of personal care compositions.

Cationic Copolymer of an Acrylamide Monomer and a Cationic Monomer

A personal care composition can include a cationic copolymer of an acrylamide monomer and a cationic monomer, wherein the copolymer has a charge density of from about 1.0 meq/g to about 3.0 meq/g. The cationic copolymer can be a synthetic cationic copolymer of acrylamide monomers and cationic monomers.

Suitable cationic polymers can include:
(i) an acrylamide monomer of the following Formula IX:

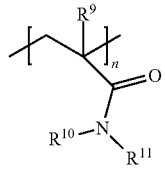

Formula IX where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and (ii) a cationic monomer conforming to Formula X:

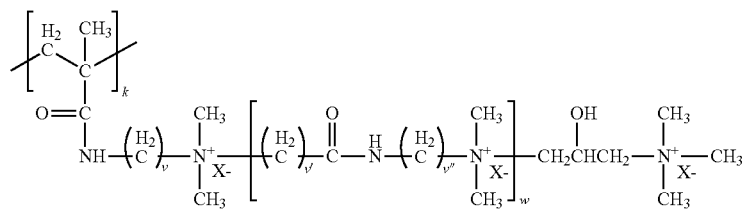

Formula X where k=1, each of v, v', and v" is independently an integer of from 1 to 6, w is zero or an integer of from 1 to 10, and X$^-$ is an anion.

A cationic monomer can conform to Formula X where k=1, v=3 and w=0, z=1 and X$^-$ is Cl$^-$ to form the following structure (Formula XI):

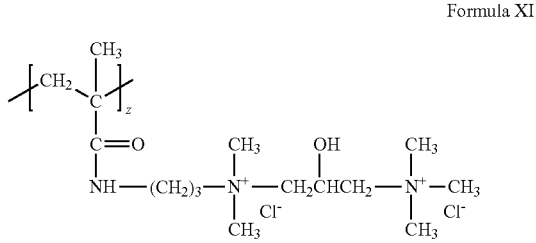

Formula XI

As can be appreciated, the above structure can be referred to as diquat.

A cationic monomer can conform to Formula X wherein v and v" are each 3, v'=1, w=1, y=1 and X⁻ is Cl⁻, to form the following structure of Formula XII:

Formula XII

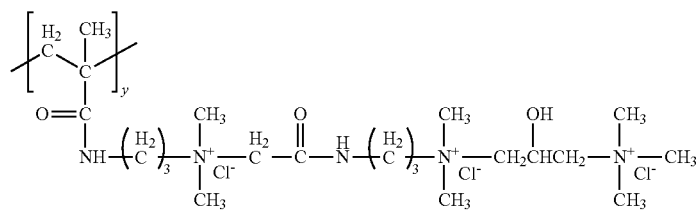

The structure of Formula XII can be referred to as triquat.

The acrylamide monomer can be either acrylamide or methacrylamide.

The cationic copolymer can be AM:TRIQUAT which is a copolymer of acrylamide and 1,3-Propanediaminium,N-[2-[[[dimethyl[3-[(2-methyl-1-oxo-2-propenyl)amino]propyl] ammonio]acetyl]amino]ethyl]2-hydroxy-N,N,N',N',N'-pentamethyl-, trichloride. AM:TRIQUAT is also known as polyquaternium 76 (PQ76). AM:TRIQUAT can have a charge density of 1.6 meq/g and a M.Wt. of 1.1 million g/mol.

The cationic copolymer can include an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer can include a cationic monomer selected from the group consisting of: trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters can be cationized esters of the (meth)acrylic acid containing a quaternized N atom. Cationized esters of the (meth)acrylic acid containing a quaternized N atom can be quaternized dialkylaminoalkyl (meth)acrylates with $C_1$ to $C_3$ in the alkyl and alkylene groups. The cationized esters of the (meth)acrylic acid containing a quaternized N atom can be selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. The cationized esters of the (meth)acrylic acid containing a quaternized N atom can be dimethylaminoethyl acrylate, which is quaternized with an alkyl halide, or with methyl chloride or benzyl chloride or dimethyl sulfate (ADAME-Quat). The cationic monomer when based on (meth)acrylamides are quaternized dialkylaminoalkyl(meth)acrylamides with $C_1$ to $C_3$ in the alkyl and alkylene groups, or dimethylaminopropylacrylamide, which is quaternized with an alkyl halide, or methyl chloride or benzyl chloride or dimethyl sulfate.

The cationic monomer based on a (meth)acrylamide can be a quaternized dialkylaminoalkyl(meth)acrylamide with $C_1$ to $C_3$ in the alkyl and alkylene groups. The cationic monomer based on a (meth)acrylamide can be dimethylaminopropylacrylamide, which is quaternized with an alkyl halide, especially methyl chloride or benzyl chloride or dimethyl sulfate.

The cationic monomer can be a hydrolysis-stable cationic monomer. Hydrolysis-stable cationic monomers can be, in addition to a dialkylaminoalkyl(meth)acrylamide, any monomer that can be regarded as stable to the OECD hydrolysis test. The cationic monomer can be hydrolysis-stable and the hydrolysis-stable cationic monomer can be selected from the group consisting of: diallyldimethylammonium chloride and water-soluble, cationic styrene derivatives.

The cationic copolymer can be a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer can be formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer can have a charge density of from about 1.1 meq/g to about 2.5 meq/g, from about 1.1 meq/g to about 2.3 meq/g, from about 1.2 meq/g to about 2.2 meq/g, from about 1.2 meq/g to about 2.1 meq/g, from about 1.3 meq/g to about 2.0 meq/g, and from about 1.3 meq/g to about 1.9 meq/g.

The cationic copolymer can have a M.Wt. from about 100 thousand g/mol to about 2 million g/mol, from about 300 thousand g/mol to about 1 8 million g/mol, from about 500 thousand g/mol to about 1.6 million g/mol, from about 700 thousand g/mol to about 1.4 million g/mol, and from about 900 thousand g/mol to about 1.2 million g/mol.

The cationic copolymer can be a trimethylammoniopropylmethacrylamide chloride-N-Acrylamide copolymer, which is also known as AM:MAPTAC. AM:MAPTAC can have a charge density of about 1.3 meq/g and a M.Wt. of about 1.1 million g/mol. The cationic copolymer can be AM:ATPAC. AM:ATPAC can have a charge density of about 1.8 meq/g and a M.Wt. of about 1.1 million g/mol.

Synthetic Polymers

A cationic polymer can be a synthetic polymer that is formed from:

i) one or more cationic monomer units, and optionally ii) one or more monomer units bearing a negative charge, and/or iii) a nonionic monomer, wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and synthetic cationic polymers which have the structure of Formula XIII:

Formula XIII

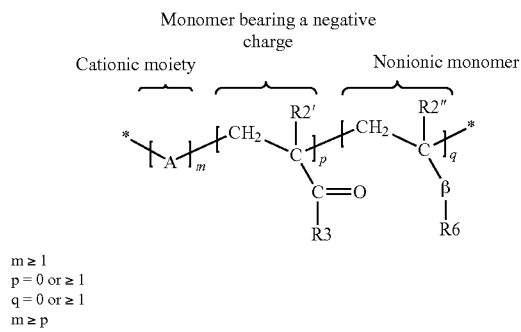

$m \geq 1$
$p = 0$ or $\geq 1$
$q = 0$ or $\geq 1$
$m \geq p$ where A, may be one or more of the following cationic moieties:

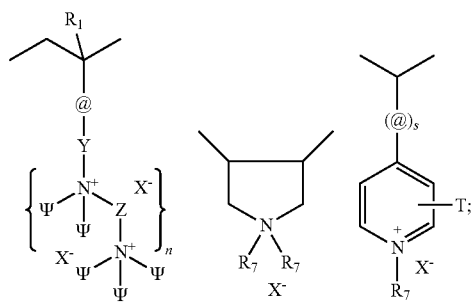

@=amido, alkylamido, ester, ether, alkyl or alkylaryl;

where Y=C1-C22 alkyl, alkoxy, alkylidene, alkyl or aryloxy;

where ψ=C1-C22 alkyl, alkyloxy, alkyl aryl or alkyl arylox;

where Z=C1-C22 alkyl, alkyloxy, aryl or aryloxy;

where R1=H, C1-C4 linear or branched alkyl;

where s=0 or 1, n=0 or ≥1;

where T and R7=C1-C22 alkyl; and where X—=halogen, hydroxide, alkoxide, sulfate or alkylsulfate.

Where the monomer bearing a negative charge is defined by R2'=H, $C_1$-$C_4$ linear or branched alkyl and R3 is:

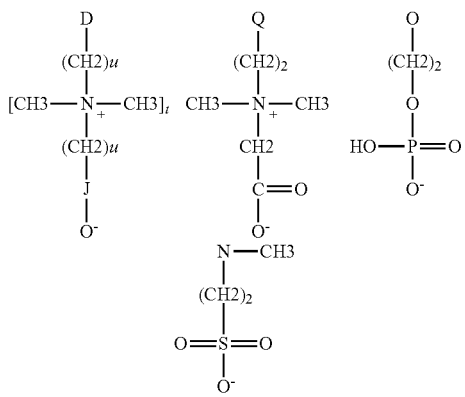

where D=O, N, or S;
where Q=$NH_2$ or O;
where u=1-6;
where t=0-1; and
where J=oxygenated functional group containing the following elements P, S, C.

Where the nonionic monomer is defined by R2"=H, $C_1$-$C_4$ linear or branched alkyl, R6=linear or branched alkyl, alkyl aryl, aryl oxy, alkyloxy, alkylaryl oxy and β is defined as

and
where G' and G" are, independently of one another, O, S or N—H and L=0 or 1.

Suitable monomers can include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of suitable cationic monomers can include dimethylaminoethyl (meth)acrylate, dimethylaminopropyl (meth)acrylate, ditertiobutylaminoethyl (meth) acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers can include quaternary monomers of formula —$NR_3^+$, wherein each R can be identical or different, and can be a hydrogen atom, an alkyl group comprising 1 to 10 carbon atoms, or a benzyl group, optionally carrying a hydroxyl group, and including an anion (counter-ion). Examples of suitable anions include halides such as chlorides, bromides, sulphates, hydrosulphates, alkylsulphates (for example comprising 1 to 6 carbon atoms), phosphates, citrates, formates, and acetates.

Suitable cationic monomers can also include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride. Additional suitable cationic monomers can include trimethyl ammonium propyl (meth) acrylamido chloride.

Examples of monomers bearing a negative charge include alpha ethylenically unsaturated monomers including a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge can include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers can include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth)acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers can also include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion ($X^-$) in association with the synthetic cationic polymers can be any known counterion so long as the polymers remain soluble or dispersible in water, in the personal care composition, or in a coacervate phase of the personal care composition, and so long as the counterions are physically and chemically compatible with the essential components of the personal care composition or do not otherwise unduly impair product performance, stability or aesthetics. Non limiting examples of suitable counterions can include halides (e.g., chlorine, fluorine, bromine, iodine), sulfate, and methylsulfate.

The cationic polymer described herein can also aid in repairing damaged hair, particularly chemically treated hair by providing a surrogate hydrophobic F-layer. The microscopically thin F-layer provides natural weatherproofing, while helping to seal in moisture and prevent further damage. Chemical treatments damage the hair cuticle and strip away its protective F-layer. As the F-layer is stripped away, the hair becomes increasingly hydrophilic. It has been found that when lyotropic liquid crystals are applied to chemically treated hair, the hair becomes more hydrophobic and more virgin-like, in both look and feel. Without being limited to any theory, it is believed that the lyotropic liquid crystal complex creates a hydrophobic layer or film, which coats the hair fibers and protects the hair, much like the natural F-layer protects the hair. The hydrophobic layer can return the hair to a generally virgin-like, healthier state. Lyotropic liquid crystals are formed by combining the synthetic cationic polymers described herein with the aforementioned anionic detersive surfactant component of the personal care composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in PCT Patent App. No. WO 94/06403 which is incorporated by reference. The synthetic polymers described herein can be formulated in a stable personal care composition that provides improved conditioning performance, with respect to damaged hair.

Cationic synthetic polymers that can form lyotropic liquid crystals have a cationic charge density of from about 2 meq/gm to about 7 meq/gm, and/or from about 3 meq/gm to about 7 meq/gm, and/or from about 4 meq/gm to about 7 meq/gm. The cationic charge density is about 6.2 meq/gm. The polymers also have a M. Wt. of from about 1,000 to about 5,000,000, and/or from about 10,000 to about 2,000,000, and/or from about 100,000 to about 2,000,000.

Cationic synthetic polymers that provide enhanced conditioning and deposition of benefit agents but do not necessarily form lytropic liquid crystals can have a cationic charge density of from about 0.7 meq/gm to about 7 meq/gm, and/or from about 0.8 meq/gm to about 5 meq/gm, and/or from about 1.0 meq/gm to about 3 meq/gm. The polymers also have a M.Wt. of from about 1,000 g/mol to about 5,000,000 g/mol, from about 10,000 g/mol to about 2,000,000 g/mol, and from about 100,000 g/mol to about 2,000,000 g/mol.

Cationic Cellulose Polymer

Suitable cationic polymers can be cellulose polymers. Suitable cellulose polymers can include salts of hydroxyethyl cellulose reacted with trimethyl ammonium substituted epoxide, referred to in the industry (CTFA) as Polyquaternium 10 and available from Dow/Amerchol Corp. (Edison, N.J., USA) in their Polymer LR, JR, and KG series of polymers. Other suitable types of cationic cellulose can include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose can include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

Additional cationic polymers are also described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)), which is incorporated herein by reference.

Techniques for analysis of formation of complex coacervates are known in the art. For example, microscopic analyses of the compositions, at any chosen stage of dilution, can be utilized to identify whether a coacervate phase has formed. Such coacervate phase can be identifiable as an additional emulsified phase in the composition. The use of dyes can aid in distinguishing the coacervate phase from other insoluble phases dispersed in the composition. Additional details about the use of cationic polymers and coacervates are disclosed in U.S. Pat. No. 9,272,164 which is incorporated by reference.

c. Liquid Carrier

As can be appreciated, personal care compositions can desirably be in the form of pourable liquid under ambient conditions. Inclusion of an appropriate quantity of a liquid carrier can facilitate the formation of a personal care composition having an appropriate viscosity and rheology. A personal care composition can include, by weight of the composition, about 20% to about 95%, by weight, of a liquid carrier, and about 60% to about 85%, by weight, of a liquid carrier. The liquid carrier can be an aqueous carrier such as water.

d. Optional Components

As can be appreciated, personal care compositions described herein can include a variety of optional components to tailor the properties and characteristics of the composition. As can be appreciated, suitable optional components are well known and can generally include any components which are physically and chemically compatible with the essential components of the personal care compositions described herein. Optional components should not otherwise unduly impair product stability, aesthetics, or performance Individual concentrations of optional components can generally range from about 0.001% to about 10%, by weight of a personal care composition. Optional components can be further limited to components which will not impair the clarity of a translucent personal care composition.

Suitable optional components which can be included in a personal care composition can include co-surfactants, deposition aids, conditioning agents (including hydrocarbon oils, fatty esters, silicones), anti-dandruff agents, suspending agents, viscosity modifiers, dyes, nonvolatile solvents or diluents (water soluble and insoluble), pearlescent aids, foam boosters, pediculocides, pH adjusting agents, perfumes, preservatives, chelants, proteins, skin active agents, sunscreens, UV absorbers, and vitamins The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of non-limiting materials that can be added to the composition herein.

e. Conditioning Agents

A personal care composition can include a silicone conditioning agent. Suitable silicone conditioning agents can include volatile silicone, non-volatile silicone, or combinations thereof. If including a silicone conditioning agent, the agent can be included from about 0.01% to about 10%, by weight of the composition, from about 0.1% to about 8%, from about 0.1% to about 5%, and/or from about 0.2% to about 3%. Examples of suitable silicone conditioning agents, and optional suspending agents for the silicone, are described in U.S. Reissue Pat. No. 34,584, U.S. Pat. Nos. 5,104,646, and 5,106,609, each of which is incorporated by reference herein. Suitable silicone conditioning agents can have a viscosity, as measured at 25° C., from about 20 centistokes ("csk") to about 2,000,000 csk, from about 1,000 csk to about 1,800,000 csk, from about 50,000 csk to about 1,500,000 csk, and from about 100,000 csk to about 1,500,000 csk.

The dispersed silicone conditioning agent particles can have a volume average particle diameter ranging from about 0.01 micrometer to about 50 micrometer. For small particle application to hair, the volume average particle diameters can range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, and/or from about 20 micrometer to about 50 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), which is incorporated herein by reference.

Silicone emulsions suitable for the personal care compositions described herein can include emulsions of insoluble polysiloxanes prepared in accordance with the descriptions provided in U.S. Pat. No. 4,476,282 and U.S. Patent Application Publication No. 2007/0276087 each of which is incorporated herein by reference. Suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol. The insoluble polysiloxane can have an average particle size within the range from about 30 nm to about 10 micron. The average particle size may be within the range from about 40 nm to about 5 micron, from about 50nm to about 1micron, from about 75 nm to about 500 nm, or about 100 nm, for example.

Other classes of silicones suitable for the personal care compositions described herein can include i) silicone fluids, including silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

Alternatively, the personal care composition can be substantially free of silicones. As used herein, substantially free of silicones means from about 0 to about 0.2 wt. %.

Organic Conditioning Materials

The conditioning agent of the personal care compositions described herein can also include at least one organic conditioning material such as oil or wax, either alone or in combination with other conditioning agents, such as the silicones described above. The organic material can be non-polymeric, oligomeric or polymeric. The organic material can be in the form of an oil or wax and can be added in the personal care formulation neat or in a pre-emulsified form. Suitable examples of organic conditioning materials can include: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

f. Emulsifiers

A variety of anionic and nonionic emulsifiers can be used in the personal care composition. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

g. Chelating Agents

The personal care composition can also comprise a chelant. Suitable chelants include those listed in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference. When related to chelants, the term "salts and derivatives thereof" means the salts and derivatives comprising the same functional structure (e.g., same chemical backbone) as the chelant they are referring to and that have similar or better chelating properties. This term include alkali metal, alkaline earth, ammonium, substituted ammonium (i.e. monoethanolammonium, diethanolammonium, triethanolammonium) salts, esters of chelants having an acidic moiety and mixtures thereof, in particular all sodium, potassium or ammonium salts. The term "derivatives" also includes "chelating surfactant" compounds, such as those exemplified in U.S. Pat. No. 5,284,972, and large molecules comprising one or more chelating groups having the same functional structure as the parent chelants, such as polymeric EDDS (ethylenediaminedisuccinic acid) disclosed in U.S. Pat. No. 5,747,440. U.S. Pat. Nos. 5,284,972 and 5,747,440 are each incorporated by reference herein. Suitable chelants can further include histidine.

Levels of an EDDS chelant or histidine chelant in the personal care compositions can be low. For example, an EDDS chelant or histidine chelant can be included at about 0.01%, by weight. Above about 10% by weight, formulation and/or human safety concerns can arise. The level of an EDDS chelant or histidine chelant can be at least about 0.01%, by weight, at least about 0.05%, by weight, at least about 0.1%, by weight, at least about 0.25%, by weight, at least about 0.5%, by weight, at least about 1%, by weight, or at least about 2%, by weight, by weight of the personal care composition.

h. Gel Network

A personal care composition can also include a fatty alcohol gel network. Gel networks are formed by combining fatty alcohols and surfactants in the ratio of from about 1:1 to about 40:1, from about 2:1 to about 20:1, and/or from about 3:1 to about 10:1. The formation of a gel network involves heating a dispersion of the fatty alcohol in water with the surfactant to a temperature above the melting point of the fatty alcohol. During the mixing process, the fatty alcohol melts, allowing the surfactant to partition into the fatty alcohol droplets. The surfactant brings water along with it into the fatty alcohol. This changes the isotropic fatty alcohol drops into liquid crystalline phase drops. When the mixture is cooled below the chain melt temperature, the liquid crystal phase is converted into a solid crystalline gel network. Gel networks can provide a number of benefits to personal care compositions. For example, a gel network can provide a stabilizing benefit to cosmetic creams and hair conditioners. In addition, gel networks can provide conditioned feel benefits to hair conditioners and personal cares.

A fatty alcohol can be included in the gel network at a level by weight of from about 0.05%, by weight, to about 14%, by weight. For example, the fatty alcohol can be included in an amount ranging from about 1%, by weight, to about 10%, by weight, and/or from about 6%, by weight, to about 8%, by weight.

Suitable fatty alcohols include those having from about 10 to about 40 carbon atoms, from about 12 to about 22 carbon atoms, from about 16 to about 22 carbon atoms, and/or about 16 to about 18 carbon atoms. These fatty alcohols can be straight or branched chain alcohols and can be saturated or unsaturated. Nonlimiting examples of fatty alcohols include cetyl alcohol, stearyl alcohol, behenyl alcohol, and mixtures thereof. Mixtures of cetyl and stearyl alcohol in a ratio of from about 20:80 to about 80:20 are suitable.

A gel network can be prepared by charging a vessel with water. The water can then be heated to about 74° C. Cetyl alcohol, stearyl alcohol, and surfactant can then be added to the heated water. After incorporation, the resulting mixture can passed through a heat exchanger where the mixture is cooled to about 35° C. Upon cooling, the fatty alcohols and surfactant crystallized can form crystalline gel network. Table 1 provides the components and their respective amounts for an example gel network composition.

To prepare the gel network pre-mix of Table 1, water is heated to about 74° C. and the fatty alcohol and gel network surfactant are added to it in the quantities depicted in Table 1. After incorporation, this mixture is passed through a mill and heat exchanger where it is cooled to about 32° C. As a result of this cooling step, the fatty alcohol, the gel network surfactant, and the water form a crystalline gel network.

Gel Network Premix Examples 1-4

Table 1 includes Examples of a gel network premix, prior to incorporation with the detersive surfactant and other components of the final personal care composition. It is intended that each of the following gel network premix examples could be incorporated as a dispersed phase into a personal care composition. A broader selection of suitable gel network premixes may be found in U.S. Pat. No. 8,361,448B2.

TABLE 1

| Ingredient | 1 | 2 | 3 | 4 |
| --- | --- | --- | --- | --- |
| Water | Q.S to 100 | Q.S to 100 | Q.S to 100 | Q.S to 100 |
| Stearyl Alcohol | 8 | 7 | 5 | 5 |
| Cetyl Alcohol | 4 | 9 | 3 | 5 |
| Sodium Laureth-1 Sulfate | 11 | | | |
| Decyl Glucoside, ≥98% (1) | | 10 | | |
| Behenyltrimethylammonium Chloride, Genamin KDMP (2) | | | 9 | 10 |

(1) available from Sigma Aldrich
(2) available from Clariant Int. Ltd.

[1]For anionic gel networks, suitable gel network surfactants above include surfactants with a net negative charge including sulfonates, carboxylates and phosphates among others and mixtures thereof.

For cationic gel networks, suitable gel network surfactants above include surfactants with a net positive charge including quaternary ammonium surfactants and mixtures thereof. For Amphoteric or Zwitterionic gel networks, suitable gel network surfactants above include surfactants with both a positive and negative charge at product usage pH including betaines, amine oxides, sultaines, amino acids among others and mixtures thereof.

Benefit Agents

A personal care composition can further include one or more benefit agents. Exemplary benefit agents include, but are not limited to, particles, colorants, perfume microcapsules, gel networks, and other insoluble skin or hair conditioning agents such as skin silicones, natural oils such as sun flower oil or castor oil. The benefit agent can be selected from the group consisting of: particles; colorants; perfume microcapsules; gel networks; other insoluble skin or hair conditioning agents such as skin silicones, natural oils such as sun flower oil or castor oil; and mixtures thereof.

i. Suspending Agent

A personal care composition can include a suspending agent at concentrations effective for suspending water-insoluble material in dispersed form in the compositions or for modifying the viscosity of the composition. Such concentrations range from about 0.05% to about 10%, and from about 0.3% to about 5.0%, by weight of the compositions. As can be appreciated however, suspending agents may not be necessary when certain glyceride ester crystals are included as certain glyceride ester crystals can act as suitable suspending or structuring agents.

Suitable suspending agents can include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Other suitable suspending agents can include crystalline suspending agents which can be categorized as acyl derivatives, long chain amine oxides, and mixtures thereof. Examples of such suspending agents are described in U.S. Pat. No. 4,741,855, which is incorporated herein by reference. Suitable suspending agents include ethylene glycol esters of fatty acids having from 16 to 22 carbon atoms. The suspending agent can be an ethylene glycol stearates, both mono and distearate, but particularly the distearate containing less than about 7% of the mono stearate. Other suitable suspending agents include alkanol amides of fatty acids, having from about 16 to about 22 carbon atoms, alternatively from about 16 to about 18 carbon atoms, suitable examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters as previously described. Long chain acyl derivatives, ethylene glycol esters of long chain carboxylic acids, long chain amine oxides, and alkanol amides of long chain carboxylic acids can also be used as suspending agents.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl dimethyl amine oxides, e.g., stearyl dimethyl amine oxide.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine Still other suitable suspending agents include di(hydrogenated tallow)phthalic acid amide, and crosslinked maleic anhydride-methyl vinyl ether copolymer.

Other suitable suspending agents include crystallizable glyceride esters. For example, suitable glyceride esters are hydrogenated castor oils such as trihydroxystearin or dihydroxystearin. Examples of additional crystallizable glyceride esters can include the substantially pure triglyceride of 12-hydroxystearic acid. 12-hydroxystearic acid is the pure form of a fully hydrogenated triglyceride of 12-hydrox-9-cis-octadecenoic acid. As can be appreciated, many additional glyceride esters are possible. For example, variations in the hydrogenation process and natural variations in castor oil can enable the production of additional suitable glyceride esters from castor oil.

j. Viscosity Modifiers

Viscosity modifiers can be used to modify the rheology of a personal care composition. Suitable viscosity modifiers can include Carbomers with tradenames Carbopol 934, Carbopol 940, Carbopol 950, Carbopol 980, and Carbopol 981, all available from B. F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Hercules, ethylene oxide and/or propylene oxide based polymers with tradenames CARBOWAX PEGs, POLYOX WASRs, and UCON FLUIDS, all supplied by Amerchol. Sodium chloride can also be used as a viscosity modifier. Other suitable rheology modifiers can include cross-linked acrylates, cross-linked maleic anhydride co-methylvinylethers, hydrophobically modified associative polymers, and mixtures thereof.

The personal care composition can have a viscosity of about 1cP to about 20,000 cP, or from about 100 cps to about 15,000cps, or from 2,500 cP to about 12,000 cP, or from 1 cP to about 5000 cP, or from about 3,500 cP to about 8,500 cP, measured at 26.6° C. with a Brookfield R/S Plus Rheometer at 2 $s^{-1}$. cP means centipoises. To suspend the microcapsules in the personal care composition the personal care composition can have a yield stress. The yield stress can be determined using Herschel-Bulkley using shear rate ranges of $10^{-2}$ to $10^{-4}$ s-1 where the yield stress is from about 0.01 to about 20 Pa, alternatively from about 0.01 to about 10 Pa, alternatively from about 0.01 to about 5 Pa.

k. Additional Optional Components

As can be appreciated, a personal care composition can include still further optional components. For example, amino acids can be included. Suitable amino acids can include water soluble vitamins such as vitamins B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their derivatives, water insoluble amino acids such as tyrosine, tryptamine, and their salts.

Anti-dandruff agents can be included. As can be appreciated, the formation of a coacervate can facilitate deposition of the anti-dandruff agent to the scalp.

A personal care composition can optionally include pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C. I. Names. The compositions can also include antimicrobial agents which are useful as cosmetic biocides and antidandruff agents including: water soluble components such as piroctone olamine, water insoluble components such as 3,4,4'-trichlorocarbanilide (trichlosan), triclocarban and zinc pyrithione.

One or more stabilizers can be included. For example, one or more of ethylene glycol distearate, citric, citrate, a preservative such as kathon, sodium benzoate, sodium salicylate and ethylenediaminetetraacetic acid ("EDTA") can be included to improve the lifespan of a personal care composition.

Test Methods

A. Visual Opaque Evaluation

Procedure

Generate a printed document using Times New Roman font where the number "3" is printed in font sizes from size 4 through size 14 in increments of 2 in a vertical column.

Fill the fluid to be evaluated in a cylindrical bottle made of transparent plastic Polyethylene Terephthalate. The cylinder should be approximately 60 mm in diameter.

Place the printed paper behind the filled bottle and position the printed number "3" in different font sizes near the center of the bottle so the "3"s are viewed through the entire bottle diameter.

Visually compare the printed "3"s of different sizes while looking through the fluid in the bottle. Hold the bottle at a comfortable distance from eyes within arms reach (for example 0.1 to 0.5m). Keep this distance similar when comparing between multiple samples.

Visually determine the smallest font size printed "3" that can be cleared read. Moving the paper or bottle slightly to attempt to see around any bubbles is acceptable.

Font Sizes 4, 6, 8, 10, 12, 14 below

.,
3
3
3
3
3

Test Results
Smallest Font Size Readable

| Tests | Acceptable Bubble Impact to Appearance | Unacceptable Bubble Impact to Appearance |
|---|---|---|
| 1 | 4 | 8 |
| 2 | 4 | 8 |
| 3 | 6 | 10 |
| 4 | 6 | 10 |

B. L* Testing for transmittance impact of air bubbles
Instrument: Konica Minolta CM-3700A Spectrophotometer
Equipment/Container for Sample: Glass Cell 20 mm CM-A99
Software: SpectraMagic™ NX Color Data Software
Procedure:
1. Connect the instrument to the PC with a USB cable
2. Connect the instrument to the AC outlet with the AC adapter
3. Turn on the PC to be used to control the instrument
4. Start the software and set it for control of the instrument
5. Turn on the instrument
6. In the software, connect with the instrument
7. Perform the zero (0%) and white (100%) calibrations
8. Fill the glass cell with the shampoo sample to be measured (fill to yellow limit line)
9. Position the filled cell in the instrument
10. Perform the L*(65) a*(65) b*(65) measurements six (6) times
11. Record average and standard deviation values for the L*(65) measurement
12. Turn off the instrument
13. Exit out of the software and turn off the PC

| L *(65) measurements quantify the impact of air bubbles on transmittance of shampoo products | | | |
|---|---|---|---|
| Product Sample: | Shampoo without bubbles | Shampoo with some bubbles | Shampoo with many bubbles |
| L *(D65) value [n = 6]: | 35.421 ± 0.002 | 39.628 ± 0.004 | 51.007 ± 0.009 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making a personal care composition, the method comprising steps of:
   providing a mixer comprising a housing comprising a first fluid inlet, a second inlet, a fluid outlet, and a the rotor rotatably connected with the housing, wherein the rotor comprises blades positioned within the housing to define cells between neighboring blades and the housing;
   preparing a personal care chassis base comprising surfactants and water;
   preparing a microcapsule composition comprising microcapsules and air;
   advancing the personal care chassis base along a flow path from the first fluid inlet toward the fluid outlet;
   transferring the microcapsule composition from the second inlet to the flow path by rotating the rotor;
   directing the air in the microcapsule composition from inside the cells toward the second inlet;
   combining the microcapsule composition with the personal care chassis base to form the personal care composition; and
   advancing the personal care composition from the fluid outlet.

2. The method of claim 1, wherein the step of directing the air further comprises forcing the air through apertures in the blades.

3. The method of claim 2, wherein the apertures can be straight through the rotor blades in a perpendicular direction to the long axis of the rotor blades.

4. The method of claim 2, wherein the apertures can be angled so as to direct a flow of air and liquid to one side of the housing.

5. The method of claim 2, wherein the apertures have a shape selected from the group consisting of round, rectangular, oval and combinations thereof.

6. The method of claim 1, wherein the step of advancing the personal care composition is done at a rate of about 50 L/min to about 150 L/min.

7. The method of claim 1, wherein the personal care composition is conveyed to a filling line.

8. The method of claim 1, wherein the personal care composition has a L* value of 0 to about 40, according to the L* Testing for transmittance impact of air bubbles method.

9. The method of claim 1, wherein the microcapsule shape is selected from the group consisting of round, bead like, lamellar or strip-like, sheet, spherical, semi-spherical, hemispherical, flat bottomed tear drop, ellipsoidal, ribbon like and any combination thereof.

10. The method of claim 1, wherein the personal care composition is further conveyed to a surge tank and then conveyed to a filling line.

11. The method of claim 1, wherein the personal care composition is conveyed through a filling nozzle.

12. The method of claim 11 wherein the filling nozzle comprises a fluid shutoff valve assembly, the fluid shutoff valve assembly having a fluid flow path defining a direction of fluid flow, the fluid shutoff valve assembly comprising:
   a fluid inlet orifice in fluid communication with a source of a fluid, the fluid inlet orifice allowing the fluid to flow in the direction of fluid flow from the source of the fluid into the fluid flow path of the fluid shutoff valve assembly;
   a fluid outlet orifice in fluid communication with the fluid flow path of the fluid shutoff valve assembly and through which the fluid may flow out of the fluid shutoff valve assembly; and
   a fluid shutoff valve in fluid communication with the fluid inlet orifice and the fluid outlet orifice, the fluid shutoff valve having a fluid blocking portion and a fluid flow-through portion, the fluid shutoff valve being moveable from a filling position wherein the fluid flow-through portion is aligned with the fluid flow path of the fluid shutoff valve assembly to a closed position wherein the fluid blocking portion is aligned with the fluid flow path of the fluid shutoff valve assembly, wherein the fluid shutoff valve is oriented such that it moves in a direction that is generally perpendicular to the direction of fluid flow at a location where the fluid shutoff valve intercepts the fluid flow path of the fluid shutoff valve assembly,
   wherein the fluid flow-through portion has an upper portion, a middle portion, and a lower portion.

13. The method of claim 12, wherein the fluid flow-through portion has a diameter at the upper portion which is larger than the diameter of the lower portion.

14. The method of claim 12, wherein the fluid flow-through portion has a diameter at the upper portion that is the same as the diameter at the lower portion.

15. The method of claim 12, wherein the upper portion of the fluid flow-through portion has the same diameter as the fluid inlet orifice.

16. The method of claim 12, wherein the lower portion of the fluid flow-through portion has the same diameter as the fluid outlet orifice.

17. The method of claim 1, wherein the personal care composition is conveyed into bottles.

18. The method of claim 1, wherein the method does not use storage tanks.

19. The method of claim 1, wherein the personal care composition comprises about 5 to about 35 wt % of a detersive surfactant selected from the group consisting of anionic surfactants, amphoteric surfactants, nonionic surfactants, and mixtures thereof.

20. The method of claim 1, wherein the personal care composition comprises about 0.05 wt % to about 3 wt % of a cationic deposition polymer.

21. The method of claim 1, wherein the personal care composition comprises about 0.05 wt % to about 10 wt % of microcapsules.

22. The method of claim 1, wherein the microcapsules are a gellan film comprising about 30 to about 40 parts of sodium alginate, about 40 to about 50 parts gellan gum, about 5 to about 10 parts polyvinyl alcohol, and about 5 to about 10 parts hydroxyl methyl cellulose sodium.

23. The method of claim 1, wherein the microcapsules comprise a material selected from the group consisting of menthol, peppermint oil, menthyl lactate, jojoba oil, Vitamin E, dyes, discrete panicles comprising anhydrous particles and an aqueous phase, perfumes and combinations thereof.

24. The method of claim 1, wherein the step of directing air further comprises forcing the air through gaps between the blades and the housing.

25. The method of claim 1, wherein the step of advancing the personal care composition is done a rate of about 1.5 L/min to about 200 L/min.

26. A method of making a personal care composition, the method comprising steps of:

providing a mixer comprising a housing comprising a first fluid inlet, a second inlet, a fluid outlet, and a rotor rotatably connected with the housing, wherein the rotor comprises blades positioned within the housing to define cells between neighboring blades and the housing;

preparing a personal care chassis base comprising surfactants and water;

preparing a microcapsule composition comprising microcapsules and an aqueous carrier;

advancing the personal care chassis base along a flow path from the first fluid inlet toward the fluid outlet;

transferring the microcapsule composition from the second inlet to the flow path by rotating the rotor; wherein air enters the microcapsule composition in the flow path;

directing the air in the microcapsule composition from inside the cells toward the second inlet;

combining the microcapsule composition with the personal care chassis base to form the personal care composition; and advancing the personal care composition from the fluid outlet.

* * * * *